US010515073B2

(12) United States Patent
Bagchi et al.

(10) Patent No.: US 10,515,073 B2
(45) Date of Patent: Dec. 24, 2019

(54) DECISION-SUPPORT APPLICATION AND SYSTEM FOR MEDICAL DIFFERENTIAL-DIAGNOSIS AND TREATMENT USING A QUESTION-ANSWERING SYSTEM

(71) Applicant: International Business Machines Corporation, Armonk, NY (US)

(72) Inventors: Sugato Bagchi, White Plains, NY (US); David A. Ferrucci, Wilton, CT (US); Anthony T. Levas, Yorktown Heights, NY (US); Erik T. Mueller, Chevy Chase, MD (US)

(73) Assignee: International Business Machines Corporation, Armonk, NY (US)

( * ) Notice: Subject to any disclaimer, the term of this patent is extended or adjusted under 35 U.S.C. 154(b) by 18 days.

(21) Appl. No.: 15/715,527

(22) Filed: Sep. 26, 2017

(65) Prior Publication Data

US 2018/0025127 A1     Jan. 25, 2018

Related U.S. Application Data

(63) Continuation of application No. 13/077,480, filed on Mar. 31, 2011, now abandoned.
(Continued)

(51) Int. Cl.
*G06F 16/2452* (2019.01)
*G06F 3/048* (2013.01)
(Continued)

(52) U.S. Cl.
CPC .......... *G06F 16/24522* (2019.01); *A61B 5/00* (2013.01); *A61B 34/10* (2016.02);
(Continued)

(58) Field of Classification Search
CPC ........ G06Q 50/22; G16H 10/00; G16H 10/20; G16H 10/40; G16H 10/60; G16H 10/65;
(Continued)

(56) References Cited

U.S. PATENT DOCUMENTS 6,292,796 B1     9/2001 Drucker et al.
6,438,533 B1 *   8/2002 Spackman ............. G06Q 10/10
                                                706/45
(Continued)

FOREIGN PATENT DOCUMENTS

CA     2843403 A1     9/2012
CA     2843405 A1     9/2012
(Continued)

OTHER PUBLICATIONS

"Answering Clinical Questions with Knowledge-Based and Statistical Techniques", Association of Computational Linguistics, vol. 33, No. 1, pp. 63-103, 2007, Dina Demner-Fushman and Jimmy Lin (Year: 2007).*
(Continued)

*Primary Examiner* — Joseph D Burgess
(74) *Attorney, Agent, or Firm* — Rakesh Roy

(57) ABSTRACT

A decision-support system for medical diagnosis and treatment comprises software modules embodied on a computer readable medium, and the software modules comprise an input/output module and a question-answering module. The method receives patient case information using the input/output module, and generates a medical diagnosis or treatment query based on the patient case information and also generates a plurality of medical diagnosis or treatment answers for the query using the question-answering module. The method also calculates numerical values for multiple medical evidence dimensions from medical evidence sources for each of the answers using the question-answer-
(Continued)

ing module and also calculates a corresponding confidence value for each of the answers based on the numerical value of each evidence dimension using the question-answering module. The method further outputs the medical diagnosis or treatment answers, the corresponding confidence values, and the numerical values of each medical evidence dimension for one or more selected medical diagnosis or treatment answers using the input/output module.

20 Claims, 16 Drawing Sheets

Related U.S. Application Data

(60) Provisional application No. 61/450,273, filed on Mar. 8, 2011.

(51) Int. Cl.
```
G06N 5/02      (2006.01)
G16H 50/70     (2018.01)
G16H 10/20     (2018.01)
G16H 50/20     (2018.01)
G06F 16/31     (2019.01)
G06F 16/93     (2019.01)
G06F 16/33     (2019.01)
G06F 16/532    (2019.01)
G06F 16/242    (2019.01)
G06F 16/2455   (2019.01)
G06F 16/903    (2019.01)
A61B 5/00      (2006.01)
G06F 19/00     (2018.01)
G06Q 50/22     (2018.01)
G06F 17/22     (2006.01)
G06F 17/24     (2006.01)
A61B 34/10     (2016.01)
G16H 70/00     (2018.01)
G16H 10/60     (2018.01)
G16H 15/00     (2018.01)
G16H 40/20     (2018.01)
G06F 17/27     (2006.01)
```
(52) U.S. Cl.
CPC .......... *G06F 3/048* (2013.01); *G06F 16/2428* (2019.01); *G06F 16/2455* (2019.01); *G06F 16/31* (2019.01); *G06F 16/334* (2019.01); *G06F 16/532* (2019.01); *G06F 16/90335* (2019.01); *G06F 16/93* (2019.01); *G06F 17/2235* (2013.01); *G06F 17/241* (2013.01); *G06F 19/00* (2013.01); *G06F 19/325* (2013.01); *G06N 5/027* (2013.01); *G06Q 50/22* (2013.01); *G16H 10/20* (2018.01); *G16H 10/60* (2018.01); *G16H 15/00* (2018.01); *G16H 40/20* (2018.01); *G16H 50/20* (2018.01); *G16H 50/70* (2018.01); *G16H 70/00* (2018.01); *G06F 17/271* (2013.01); *Y02A 90/22* (2018.01); *Y02A 90/26* (2018.01)

(58) Field of Classification Search
CPC ........ G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 40/00; G16H 40/20; G16H 40/40; G16H 40/60; G16H 40/63; G16H 40/67; G16H 50/00; G16H 70/00; G16H 70/20; G16H 70/40; G16H 70/60; G16H 80/00
See application file for complete search history.

(56) References Cited

U.S. PATENT DOCUMENTS

| | | | |
|---|---|---|---|
| 6,527,713 B2* | 3/2003 | Iliff | G06Q 50/22 |
| | | | 600/300 |
| 7,149,756 B1 | 12/2006 | Schmitt et al. | |
| 7,197,497 B2 | 3/2007 | Cossock | |
| 7,225,183 B2 | 5/2007 | Gardner | |
| 7,344,496 B2 | 3/2008 | Iliff | |
| 7,757,163 B2 | 7/2010 | Doganata et al. | |
| 8,032,398 B1 | 10/2011 | Kelly et al. | |
| 8,200,656 B2 | 6/2012 | Brown et al. | |
| 8,275,803 B2 | 9/2012 | Brown et al. | |
| 8,280,838 B2 | 10/2012 | Ferrucci et al. | |
| 8,301,438 B2 | 10/2012 | Ferrucci et al. | |
| 8,332,394 B2 | 12/2012 | Fan et al. | |
| 8,510,327 B2 | 8/2013 | Boguraev et al. | |
| 8,560,300 B2 | 10/2013 | Ferrucci et al. | |
| 8,738,362 B2 | 5/2014 | Ferrucci et al. | |
| 8,738,617 B2 | 5/2014 | Brown et al. | |
| 8,892,550 B2 | 11/2014 | Chu-Carroll et al. | |
| 8,898,159 B2 | 11/2014 | Brown et al. | |
| 8,972,321 B2 | 3/2015 | Ferrucci et al. | |
| 8,972,440 B2 | 3/2015 | Boguraev et al. | |
| 9,002,773 B2 | 4/2015 | Bagchi et al. | |
| 9,020,805 B2 | 4/2015 | Boguraev et al. | |
| 9,153,142 B2 | 10/2015 | Bagchi et al. | |
| 9,189,541 B2 | 11/2015 | Brown et al. | |
| 9,317,586 B2 | 4/2016 | Chu-Carroll et al. | |
| 9,454,603 B2 | 9/2016 | Boguraev et al. | |
| 9,495,481 B2 | 11/2016 | Brown et al. | |
| 9,569,724 B2 | 2/2017 | Ferucci et al. | |
| 9,600,601 B2 | 3/2017 | Brown et al. | |
| 9,798,800 B2 | 10/2017 | Duboue et al. | |
| 9,864,818 B2 | 1/2018 | Brown et al. | |
| 9,965,509 B2 | 5/2018 | Brown et al. | |
| 2003/0105638 A1 | 6/2003 | Taira | |
| 2004/0122702 A1 | 6/2004 | Sabol et al. | |
| 2004/0243560 A1 | 12/2004 | Broder et al. | |
| 2005/0010444 A1 | 1/2005 | Iliff | |
| 2006/0015498 A1 | 1/2006 | Sarmiento et al. | |
| 2006/0160054 A1 | 7/2006 | Onishi et al. | |
| 2007/0067293 A1 | 3/2007 | Yu | |
| 2008/0052122 A1 | 2/2008 | Iliff | |
| 2008/0059453 A1 | 3/2008 | Laderman | |
| 2008/0082357 A1 | 4/2008 | Schmitt et al. | |
| 2008/0201280 A1 | 8/2008 | Martin et al. | |
| 2008/0301120 A1 | 12/2008 | Zhu et al. | |
| 2009/0030856 A1 | 1/2009 | Arena et al. | |
| 2009/0162824 A1 | 6/2009 | Heck | |
| 2009/0292557 A1 | 11/2009 | Sirohey et al. | |
| 2010/0076780 A1 | 3/2010 | Mahesh et al. | |
| 2010/0131438 A1 | 5/2010 | Pandya et al. | |
| 2010/0153332 A1 | 6/2010 | Rollins et al. | |
| 2010/0235378 A1 | 9/2010 | Armstrong et al. | |
| 2010/0280847 A1 | 11/2010 | Schaffer | |
| 2010/0318549 A1* | 12/2010 | Mayr | G16H 10/60 |
| | | | 707/759 |
| 2011/0004588 A1 | 1/2011 | Leitersdorf et al. | |
| 2011/0055190 A1 | 3/2011 | Alexander | |
| 2011/0055240 A1 | 3/2011 | Li et al. | |
| 2011/0078192 A1 | 3/2011 | Murdock, IV | |
| 2011/0125734 A1 | 5/2011 | Duboue et al. | |
| 2012/0005148 A1 | 1/2012 | Horvitz et al. | |
| 2012/0041950 A1 | 2/2012 | Koll et al. | |
| 2012/0078062 A1 | 3/2012 | Bagchi et al. | |
| 2012/0078837 A1 | 3/2012 | Bagchi et al. | |
| 2012/0084112 A1 | 4/2012 | Bagchi et al. | |
| 2012/0131016 A1 | 5/2012 | Brown et al. | |
| 2013/0041921 A1 | 2/2013 | Cooper et al. | |
| 2014/0142920 A1 | 5/2014 | Chu-Carroll et al. | |
| 2017/0154043 A1 | 6/2017 | Brown et al. | |

(56) References Cited

U.S. PATENT DOCUMENTS

| | | | |
|---|---|---|---|
| 2018/0144066 A1 | 5/2018 | Brown et al. | |
| 2018/0246890 A1 | 8/2018 | Brown et al. | |

FOREIGN PATENT DOCUMENTS

| | | | |
|---|---|---|---|
| IN | 6102CHENP2013 A | 9/2014 | |
| IN | 6113CHENP2013 A | 9/2014 | |
| KR | 101555114 B1 | 9/2015 | |
| KR | 101634425 B1 | 6/2016 | |
| WO | 200150330 A1 | 7/2001 | |
| WO | 2012122196 A2 | 9/2012 | |
| WO | 2012122198 A1 | 9/2012 | |

OTHER PUBLICATIONS

Barnett, G.O., Cimino, J.J., Hupp, J.A., Hoffer, E.P. DXplain: An evolving diagnostic decision-support system. JAMA 258, 1 (1987), 67-74.
Berner, E.S. Diagnostic Decision Support Systems: Why aren't they used more and what can we do about it? AMIA Annu. Symp. Proc. 2006 (2006), 1167-1168.
Sim, I., Gorman, P., Greenes, R.A., Haynes, R.B., Kaplan, B., Lehmann, H. and Tang, P.C. Clinical decision support systems for the practice of evidence-based medicine. J. Am. Med. Inform. Assoc. 8, 6 (2001), 527-534.
Cannon, D.S. and Allen, S.N. A comparison of the effects of computer and manual reminders on compliance with a mental health clinical practice guideline. Journal of the American Medical Informatics Association 7, 2 (2000), 196-203.
Warner, H.R., Haug, P., Bouhaddou, O., Lincoln, M., Warner, H., Sorenson, D., Williamson, J.W. and Fan, C. Iliad as an expert consultant to teach differential diagnosis. In Proc. Annu. Symp. Comput. Appl. Med. Care. (1988), 371-376.
Friedman, C.P., Elstein, A.S., Wolf, F.M., Murphy, G.C., Franz, T.M., Heckerling, P.S., Fine, P.L., Miller, T.M. and Abraham, V. Enhancement of clinicians' diagnostic reasoning by computer-based consultation: A multisite study of 2 systems. JAMA 282, 19 (1999), 1851-1856.
Myers, J.D. The background of INTERNIST-I and QMR. In Proceedings of ACM Conference on History of Medical Informatics (1987), 195-197.
Ramnarayan, P., Tomlinson, A., Rao, A., Coren, M., Winrow, A. and Britto, J. Isabel: A web-based differential diagnostic aid for paediatrics: Results from an initial performance evaluation. Archives of Disease in Childhood 88, 5 (2003), 408-413.
Ramnarayan, P., Roberts, G.C., Coren, M., Nanduri, V., Tomlinson, A., Taylor, P.M., Wyatt, J.C. and Britto, J.F. Assessment of the potential impact of a reminder system on the reduction of diagnostic errors: A quasi-experimental study. BMC Med. Inform. Decis. Mak. 6, 22 (2006).
Selker, H.P., Beshansky, J.R., Griffith, J.L., Aufderheide, T.P., Ballin, D.S., Bernard, S.A., Crespo, S.G., Feldman, J.A., Fish, S.S., Gibler, W.B., Kiez, D.A., McNutt, R.A., Moulton, A.W., Ornato, J.P., Podrid, P.J., Pope, J.H., Salem, D.N., Sayre, M.R. and Woolard, R.H. Use of the acute cardiac ischemia time-insensitive predictive instrument (ACI-TIPI) to assist with triage of patients with chest pain or other symptoms suggestive of acute cardiac ischemia: A multicenter, controlled clinical trial. Annals of Internal Medicine 129, 11 (1998), 845-855.
Shortliffe, T. Medical thinking: What should we do? In Proceedings of Medical Thinking: What Do We Know? A Review Meeting (2006). http://www.openclinical.org/medicalThinking2006Summary2. html.
U.S. Appl. No. 13/077,480, Office Action Communication dated Jan. 17, 2013, pp. 1-11.
U.S. Appl. No. 13/077,480, Office Action Communication dated Jun. 10, 2013, pp. 1-14.
U.S. Appl. No. 13/077,480, Advisory Action dated Sep. 11, 2013, pp. 1-5.
International Application No. PCT/US2012/027936, PCT International Search Report and Written Opinion dated Oct. 1, 2013, pp. 1-9.
International Application No. PCT/US2012/027936, PCT International Search Report and Written Opinion dated Oct. 8, 2013, pp. 1-6.
U.S. Appl. No. 13/077,480, Office Action Communication dated Apr. 9, 2014, pp. 1-14.
Appendix P: List of IBM Patents or Applications Treated As Related, Dated May 26, 2014, p. 1.
Demner-Fushman et al. "Answering Clinical Questions with Knowledge-Based and Statistical Techniques" Association for Computational Linguistics, vol. 33, No. 1, 2007, pp. 1-41.
Kathleen Ann McKibbon ("The Effect of Risk Attitude and Uncertainty Comfort on Primary Care Physicians' Use of Electronic Information Resources" 2005).
PCT International Search Report, International Appln. No. PCT/US2012/027942, dated Aug. 21, 2012, pp. 1-10.
O'Sullivan et al. "Automatic indexing and retrieval of encounter-specific evidence for point-of-care support" Journal of Biomedical Informatics, vol. 43, Mar. 2010, pp. 623-631.
Office Action Communication U.S. Appl. No. 13/077,464, dated Nov. 14, 2013, pp. 1-24.
Office Action Communication U.S. Appl. No. 13/077,464, dated Mar. 7, 2014, pp. 1-22.
Advisory Action Communication U.S. Appl. No. 13/077,464, dated May 29, 2014, pp. 1-5.
David Ferrucci et al., "Building Watson: An Overview of the Deep QA Project", Copyright © 2010, Association for the Advancement of Artificial Intelligence. pp. 1-21, Fall, 2010.
Mark Graber, "Diagnostic Error in Internal Medicine", Arch Intern Med/vol. 165, Jul. 11, 2005 www.archinternmed.com., pp. 1-7.
Robert Trowbridge, MD, Chapter 53. Clinical Decision Support Systems, http://www.ahrq.gov/clinic/ptsafety/chap53.htm, Apr. 10, 2012., pp. 589-194.
David Ferrucci et al., IBM Research Report, "Towards the Open Advancement of Question Answering Systems", RC24789 Computer Science, Apr. 22, 2009, pp. 1-29.
David Ferrucci et al., IBM Research Report, "Watson: Beyond Jeopardy", RC25270 Computer Science, Jun. 2, 2011, pp. 1-11.
Unified Medical Language System® (UMLS®), UMLS MetaMap: http://www.nlm.nih.Gov/research/umls/implementation_resources/metamap.html, Apr. 12, 2012, pp. 1-2.
hittp://www.isabelhealthcare.com/home/, Apr. 16, 2012, p. 1.
www.autonomyhealth.com, Apr. 16, 2012, p. 1.
Office Action Communication, U.S. Appl. No. 13/448,607 dated Nov. 25, 2013, pp. 1-21.
Office Action Communication, U.S. Appl. No. 13/448,607 dated Jun. 2, 2014, pp. 1-18.
Office Action Communication, U.S. Appl. No. 13/077,480 dated Sep. 3, 2014, pp. 1-12.
U.S. Appl. No. 13/448,607, Office Action Communication dated Oct. 3, 2014, 25 pages.
U.S. Appl. No. 13/077,464, Office Action Communication dated Sep. 22, 2014, pp. 1-16.
U.S. Appl. No. 13/077,480, Advisory Action dated Oct. 20, 2014, pp. 1-7.
U.S. Appl. No. 13/077,464, Notice of Allowance dated Nov. 24, 2014, 5 pages.
U.S. Appl. No. 13/077,480, Office Action Communication dated Dec. 10, 2014, 13 pages.
U.S. Appl. No. 13/448,607, Office Action Communication dated Mar. 26, 2015, 28 pages.
U.S. Appl. No. 13/077,480, Office Action Communication dated Apr. 17, 2015, 9 pages.
10-2013-7025364, Korean Office Action dated Feb. 17, 2015, 8 pages.
U.S. Appl. No. 13/448,607, Notice of Allowance dated May 28, 2015, 6 pages.
U.S. Appl. No. 13/077,480, Examiner's Answer dated Jan. 15, 2016, 12 pages.
U.S. Appl. No. 13/077,480, Board's Decision dated Aug. 14, 2017, 14 pages.

(56) References Cited

OTHER PUBLICATIONS

U.S. Appl. No. 13/077,480, Advisory Action dated May 28, 2015, 3 pages.
U.S. Appl. No. 13/448,607, Office Action Communication dated Nov. 25, 2013, 19 pages.
U.S. Appl. No. 13/448,607, Office Action Communication dated Jun. 2, 2014, 17 pages.
U.S. Appl. No. 13/448,607, Advisory Action dated Aug. 14, 2014, 3 pages.
U.S. Appl. No. 13/077,464, Office Action Communication dated Nov. 14, 2013, 17 pages.
U.S. Appl. No. 13/077,464, Office Action Communication dated Mar. 7, 2014, 22 pages.
U.S. Appl. No. 13/077,464, Advisory Action dated May 29, 2014, 5 pages.
Cao et al., "Askhermes: An Online Answering System for Complex Clinical Questions," J Biomed Inform, Jan. 2011, pp. 1-32.
Mendonca et al., "Answering Information Needs in Workflow," Department of Biomedical Informatics, Columbia University, NY, 2005, pp. 1-8.
Yu et al., "Automatically Extracting Information Needs from Ad Hoc Clinical Questions," Departments of Health Sciences and Computer Science, Medical Informatics, University of Wisconsin—Milwaukee, 2008, pp. 96-100.
Kasneci et al., "NAGA: Searching and Ranking Knowledge," IEEE 24th International Conference on Data Engineering (ICDE), 2008, p. 953-962.
Simulconsult, "A Simultaneous Consult on Your Patient's Diagnosis," SimulConsult, p. 1-2, https://www.simulconsult.com/, Accessed on Mar. 5, 2019.

\* cited by examiner

| | IBM Watson Medical | |
|---|---|---|
| ◀ Patients | Patient Record | |
| Samantha Darren - March 3, 2011 | | |
| History of present illness | | |
| The patient has a confirmed case of uveitis.<br>She reports a family history of arthritis. | | |
| Present Illness    Family history | | |
| Question | | |
| What disease or condition can cause uveitis in a patient with a family history of arthritis? | | |
| Answer | Evidence   Ask Watson | |
| Bechet's Disease | ▭▭▭ | 55% |
| Juvenile Rheumatoid Arthritis | ▭▭ | 36% |
| Ankylosing Spondylitis | ▭ | 26% |
| Sarcoidosis | ▭ | 16% |
| Rheumatoid Arthritis | ▫ | 11% |
| IBMWATSON | | Medical |

- 500 (window)
- 502 (Patient Record)
- 506 (history text)
- 508 (Question)
- 510 (Ask Watson)
- 512 (Evidence)
- 514 (answer list)

FIG. 9

```
┌─────────────────────────────────────────────┐
│ ○ ○ ○         IBM Watson Medical            │──500
├─────────────────────────────────────────────┤
│ ◄Patients       Patient Record              │──502
├─────────────────────────────────────────────┤
│ ▓ Samantha Darren - March 3, 2011           │
├─────────────────────────────────────────────┤
│ History of present illness                  │
├─────────────────────────────────────────────┤
│ The patient has a confirmed case of uveitis.│
│ She reports a family history of arthritis.  │
│ On physical examination a circular rash is  │──506
│ observed. She complains of fever and        │
│ headache.                                   │
│                                             │
│  ● Present illness   Family history  Finding│
├─────────────────────────────────────────────┤
│ Question                                    │
├─────────────────────────────────────────────┤
│ What disease or condition can cause uveitis │
│ in a patient with circular rash, fever,     │──508
│ headache and family history of arthritis?   │
├─────────────────────────────────────────────┤
│                    ( Evidence )(Ask Watson) │──510
│ Answer                                      │──512
├─────────────────────────────────────────────┤
│ Lyme Disease                    ▓▓▓▓  62%   │
│ Systemic Lupus Erythematosus    ▓    17%    │
│ Juvenile Rheumatoid Arthritis   ▓    12%    │──514
│ Erythema Migrans                ░     7%    │
│ Rocky Mountain Spotted Fever    ░     6%    │
│                                             │
├─────────────────────────────────────────────┤
│ IBMWATSON                           Medical │
└─────────────────────────────────────────────┘
```

FIG. 10

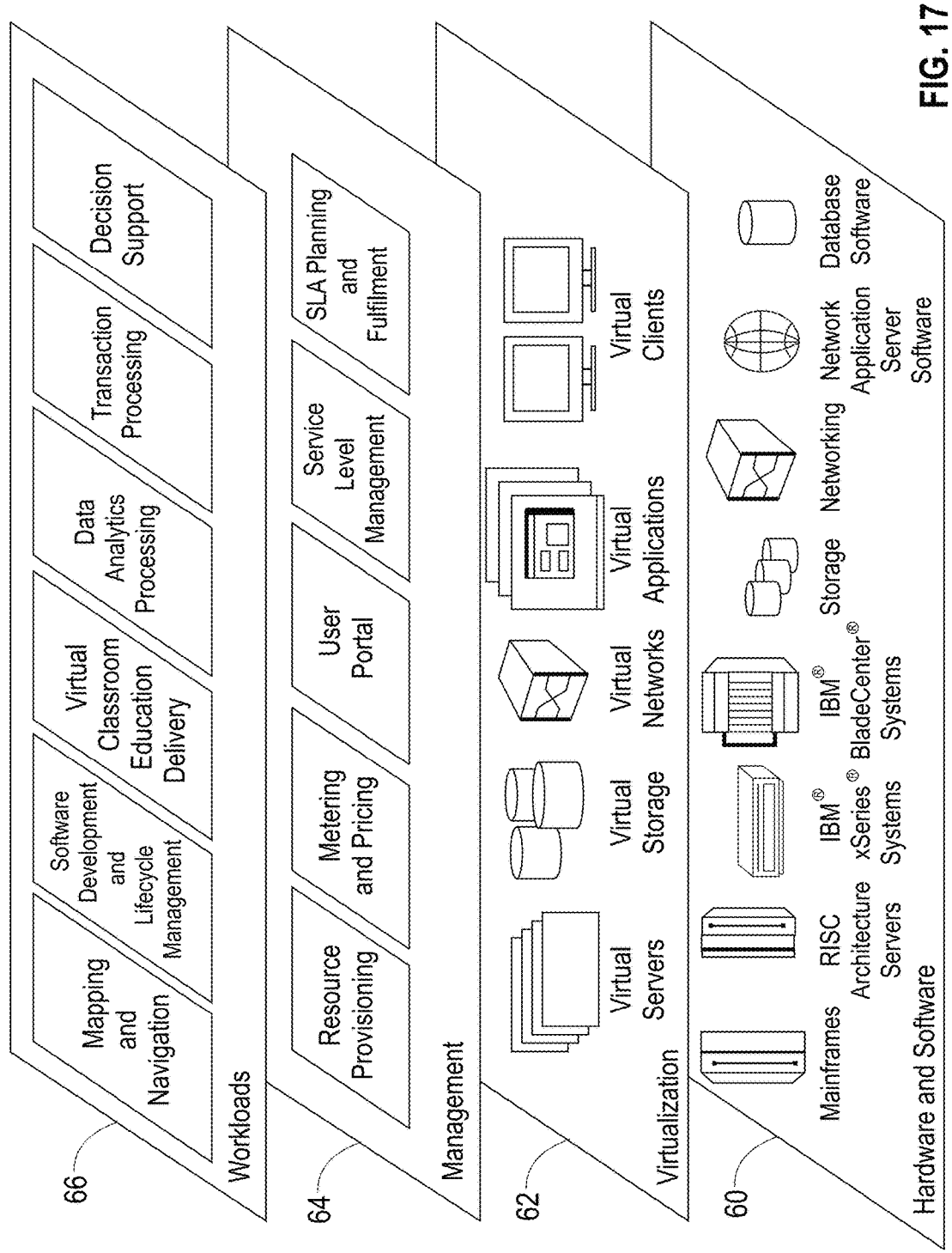

DECISION-SUPPORT APPLICATION AND SYSTEM FOR MEDICAL DIFFERENTIAL-DIAGNOSIS AND TREATMENT USING A QUESTION-ANSWERING SYSTEM

CROSS-REFERENCE TO RELATED APPLICATIONS

The present invention claims the benefit under 35 U.S.C. § 120 as a Continuation of presently pending U.S. patent application Ser. No. 13/077,480 filed on Mar. 31, 2011, the entire teachings of which are incorporated herein by reference, which also claims priority to U.S. Provisional Application Ser. No. 61/450,273 filed on Mar. 8, 2011, the complete disclosure of which, in its entirety, is herein incorporated by reference.

BACKGROUND

The embodiments herein relate to using a question-answering system to support a human expert in problem solving in a particular domain, and more specifically to a decision-support application and system for problem solving using a question-answering system.

Decision-support systems exist in many different industries where human experts require assistance in retrieving and analyzing information. An example that will be used throughout this application is a diagnosis system employed in the health care industry.

Diagnosis systems can be classified into systems that use structured knowledge, systems that use unstructured knowledge, and systems that use clinical decision formulas, rules, trees, or algorithms. The earliest diagnosis systems used structured knowledge or classical, manually constructed knowledge bases. The Internist-I system developed in the 1970s uses disease-finding relations and disease-disease relations, with associated numbers such as sensitivity, the fraction of patients with a disease who have finding (Myers, J. D. The background of INTERNIST-I and QMR. *In Proceedings of ACM Conference on History of Medical Informatics* (1987), 195-197).

The MYCIN system for diagnosing infectious diseases, also developed in the 1970s, uses structured knowledge in the form of production rules, stating that if certain facts are true, then one can conclude certain other facts with a given certainty factor (Buchanan, B. G. and Shortliffe, E. H. (Eds.) *Rule-Based Expert Systems: The MYCIN Experiments of the Stanford Heuristic Programming Project*. Addison-Wesley, Reading, Mass., 1984). DXplain, developed starting in the 1980s, uses structured knowledge similar to that of Internist-I, but adds a hierarchical lexicon of findings (Barnett, G. O., Cimino, J. J., Hupp, J. A., Hoffer, E. P. DXplain: An evolving diagnostic decision-support system. *JAMA* 258, 1 (1987), 67-74).

Iliad, developed starting in the 1990s, adds more sophisticated probabilistic reasoning. Each disease has an associated a priori probability of the disease (in the population for which Iliad was designed), and a list of findings, along with the fraction of patients with the disease who have the finding (sensitivity), and the fraction of patients without the disease who have the finding (1-specificity) (Warner, H. R., Haug, P., Bouhaddou, O., Lincoln, M., Warner, H., Sorenson, D., Williamson, J. W. and Fan, C. ILIAD as an expert consultant to teach differential diagnosis. *In Proc. Annu. Symp. Comput. Appl. Med. Care.* (1988), 371-376). DiagnosisPro (http://en.diagnosispro.com) is a structured knowledge base that can be queried and browsed online.

In 2000, diagnosis systems using unstructured knowledge started to appear. These systems use some structuring of knowledge. For example, entities such as findings and disorders may be tagged in documents to facilitate retrieval. ISABEL uses Autonomy information retrieval software and a database of medical textbooks to retrieve appropriate diagnoses given input findings (Ramnarayan, P., Tomlinson, A., Rao, A., Coren, M., Winrow, A. and Britto, J. ISABEL: A web-based differential diagnostic aid for paediatrics: Results from an initial performance evaluation. *Archives of Disease in Childhood* 88, 5 (2003), 408-413).

Autonomy Auminence uses the Autonomy technology to retrieve diagnoses given findings and organizes the diagnoses by body system (http://www.autonomyhealth.com). First CONSULT allows one to search a large collection of medical books, journals, and guidelines by chief complaints and age group to arrive at possible diagnoses (http://www.firstconsult.com). PEPID DDX is a diagnosis generator based on PEPID's independent clinical content (http://www.pepid.com/products/ddx/).

Clinical decision rules have been developed for a number of disorders, and computer systems have been developed to help practitioners and patients apply these rules. The Acute Cardiac Ischemia Time-Insensitive Predictive Instrument (ACI-TIPI) takes clinical and ECG features as input and produces probability of acute cardiac ischemia as output (Selker, H. P., Beshansky, J. R., Griffith, J. L., Aufderheide, T. P., Ballin, D. S., Bernard, S. A., Crespo, S. G., Feldman, J. A., Fish, S. S., Gibler, W. B., Kiez, D. A., McNutt, R. A., Moulton, A. W., Ornato, J. P., Podrid, P. J., Pope, J. H., Salem, D. N., Sayre, M. R. and Woolard, R. H. Use of the acute cardiac ischemia time-insensitive predictive instrument (ACI-TIPI) to assist with triage of patients with chest pain or other symptoms suggestive of acute cardiac ischemia: A multicenter, controlled clinical trial. *Annals of Internal Medicine* 129, 11 (1998), 845-855). For example, ACI-TIPI is incorporated into commercial heart monitors/defibrillators.

The CaseWalker system uses a four-item questionnaire to diagnose major depressive disorder (Cannon, D. S. and Allen, S. N. A comparison of the effects of computer and manual reminders on compliance with a mental health clinical practice guideline. *Journal of the American Medical Informatics Association* 7, 2 (2000), 196-203). The PKC Advisor provides guidance on 98 patient problems such as abdominal pain and vomiting (http://www.pkc.com/software/advisor/).

The strengths of current diagnosis systems are that they can improve clinicians' diagnostic hypotheses (Friedman, C. P., Elstein, A. S., Wolf, F. M., Murphy, G. C., Franz, T. M., Heckerling, P. S., Fine, P. L., Miller, T. M. and Abraham, V. Enhancement of clinicians' diagnostic reasoning by computer-based consultation: A multisite study of 2 systems. *JAMA* 282, 19 (1999), 1851-1856), and can help clinicians avoid missing important diagnoses (Ramnarayan, P., Roberts, G. C., Coren, M., Nanduri, V., Tomlinson, A., Taylor, P. M., Wyatt, J. C. and Britto, J. F. Assessment of the potential impact of a reminder system on the reduction of diagnostic errors: A quasi-experimental study. *BMC Med. Inform. Decis. Mak.* 6, 22 (2006)).

Current diagnosis systems are not widely used (Berner, E. S. Diagnostic Decision Support Systems: Why aren't they used more and what can we do about it? *AMIA Annu. Symp. Proc.* 2006 (2006), 1167-1168, hereinafter referred to as Berner, 2006) because the systems suffer from limitations that prevent them from being integrated into the day-to-day operations of health organizations (Coiera, E. *Guide to Health Informatics* (Second Edition). Hodder Arnold, 2003; and Shortliffe, T. Medical thinking: What should we do? *In Proceedings of Medical Thinking: What Do We Know? A Review Meeting* (2006), http://www.openclinical.org/medicalThinking2006Summary2.html, hereinafter referred to as Shortliffe, 2006).

Many different healthcare workers may see a patient, and patient data may be scattered across many different computer systems in both structured and unstructured form. Also, the systems are difficult to interact with (Berner, 2006; Shortliffe, 2006). The entry of patient data is difficult, the list of diagnostic suggestions may be too long, and the reasoning behind diagnostic suggestions is not always transparent. Further, the systems are not focused enough on next actions, and do not help the clinician figure out what to do to help the patient (Shortliffe, 2006). The systems are also unable to ask the practitioner for missing information that would increase confidence in a diagnosis, and they are not always based on the latest, high-quality medical evidence and have difficulty staying up-to-date (Sim, I., Gorman, P., Greenes, R. A., Haynes, R. B., Kaplan, B., Lehmann, H. and Tang, P. C. Clinical decision support systems for the practice of evidence-based medicine. *J. Am. Med. Inform. Assoc.* 8, 6 (2001), 527-534).

In view of these issues, the disclosed embodiments herein provide an improved medical diagnosis system.

SUMMARY

One exemplary method embodiment herein provides a decision-support system for medical diagnosis and treatment. The system comprises software modules embodied on a computer readable medium, and the software modules comprise an input/output module and a question-answering module. The method receives patient case information using the input/output module and generates a medical diagnosis or treatment query based on the patient case information and also generates a plurality of medical diagnosis or treatment answers for the query using the question-answering module. The method also calculates numerical values for multiple medical evidence dimensions from medical evidence sources for each of the answers using the question-answering module, and also calculates a corresponding confidence value for each of the answers based on the numerical value of each evidence dimension using the question-answering module. The method further outputs the medical diagnosis or treatment answers, the corresponding confidence values, and the numerical values of each medical evidence dimension for one or more selected medical diagnosis or treatment answers using the input/output module.

An exemplary system embodiment system comprises a first repository maintaining patient case information, a computer processor operatively connected to the first repository, and a second repository operatively connected to the computer processor. The computer processor is configured to receive the patient case information from the first repository, to generate a medical diagnosis or treatment query based on the patient case information, and to generate a plurality of medical diagnosis or treatment answers for the query. The computer processor is also configured to calculate numerical values for multiple medical evidence dimensions from medical evidence sources for each of the answers and to calculate corresponding confidence values for each of the answers based on the numerical values of each medical evidence dimension. The computer processor is further configured to output the medical queries, the medical answers, the corresponding confidence values, and the numerical values of each medical evidence dimension to the second repository.

An additional embodiment herein comprises a computer program product comprising a computer readable storage medium storing computer readable program code comprising instructions executable by a computerized device. The computer program code comprises an input/output module receiving patient case information, a patient case analysis module analyzing the patient case information in order to identify semantic concepts, a question generation module generating a medical diagnosis or treatment query from the semantic concepts, and a question-answering module generating a plurality of medical diagnosis or treatment answers for the query. The question-answering module calculates numerical values for multiple medical evidence dimensions from medical evidence sources for each of the answers, calculates corresponding confidence values for each of the answers based on the numerical value of each medical evidence dimension using the question-answering module. Also, the input/output module outputs the medical diagnosis or treatment queries, the medical diagnosis or treatment answers, the corresponding confidence values, and the numerical values for multiple medical evidence dimensions.

BRIEF DESCRIPTION OF THE SEVERAL VIEWS OF THE DRAWINGS

FIG. 9 is a schematic diagram illustrating an embodiment herein applied to the medical domain;

FIG. 10 is a schematic diagram illustrating an embodiment herein applied to the medical domain;

FIG. 17 is a schematic diagram illustrating an abstraction model layers according to an embodiment herein.

DETAILED DESCRIPTION

The following disclosure explains a decision-support application for problem solving in a particular domain. The domain can be specific, for example differential diagnosis in the medical domain, as will be discussed below, or broader ranging. The objective of the decision-support application is to inform a problem solving process based on relevant contextual information for the problem, as described in a target case. This case input information can be structured, unstructured or in other forms. Decision support is provided using a question-answering system that takes in questions or queries and returns a list of answers and associated confidences.

When the method refers to a question-answering system, it means a system that can take an input query expressed in many possible forms, including natural language, structured language or many other means. Note, that an answer need not be limited to be a single "atomic" concept (such as person, place or thing), but may be a complex entity. Some examples of complex entities are elaborate explanations reached through complex reasoning or a sequence of process steps required to achieve the intended goal of the user. Embodiments herein can be applied to a variety of domains involving complex systems that require human experts to solve problems. For example, a detailed explanation is provided for a decision support application targeting differential diagnosis and treatment in the medical domain (as an example of one of many domains). As would be understood by those ordinarily skilled in the art, this system can be used for other complex systems as well.

One embodiment herein allows "mixed-initiative" dialog. For example, the user may ask queries and get answers from the application. Additionally, the application can automatically provide "push" notifications (e.g., alerting of some significant change) to the user or ask queries of the user that would help change the systems confidence in answers that it provides. In effect, the system can continuously monitor relevant case input as well as take directed queries regarding a specific case.

Figure 1:
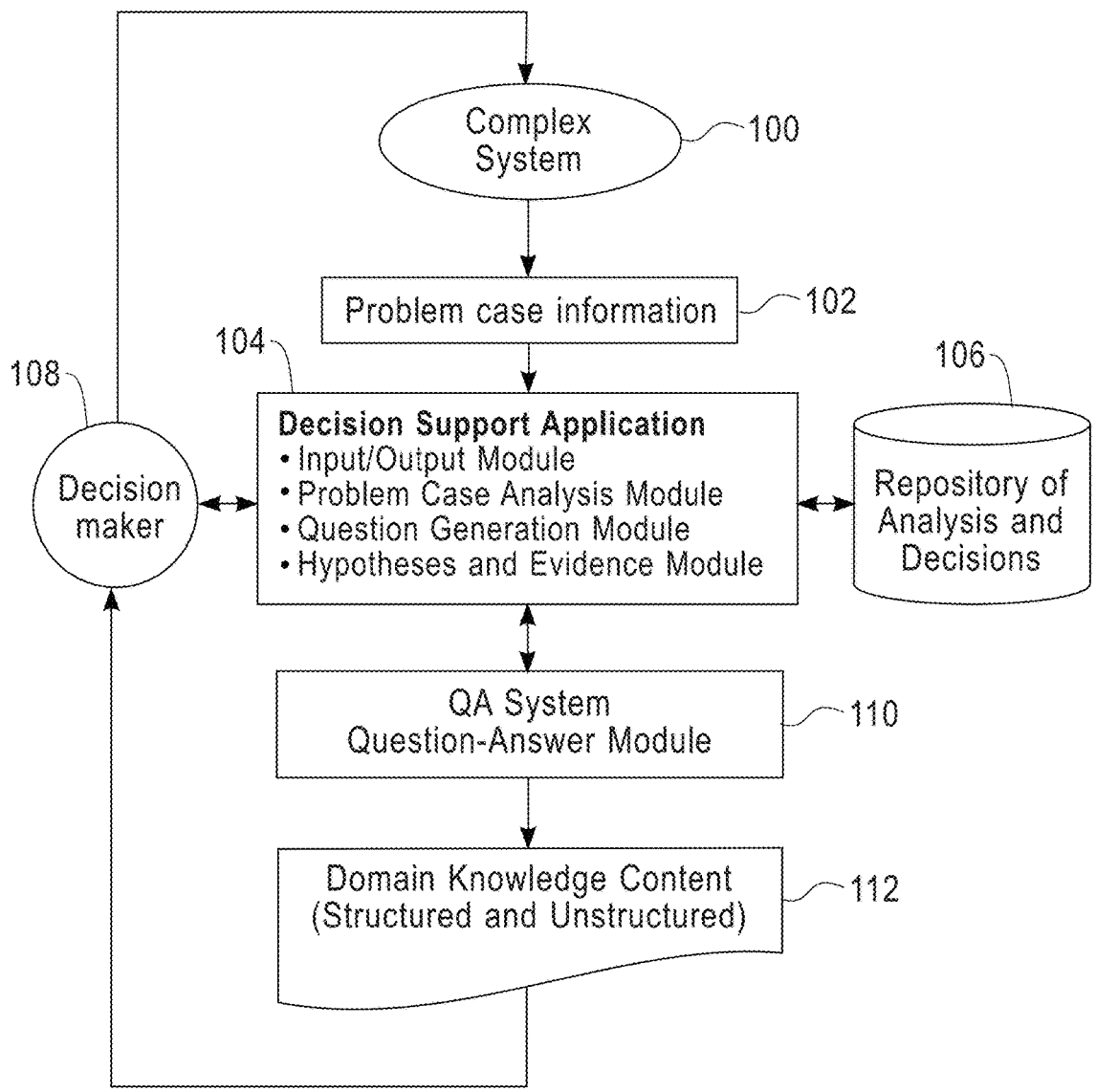
FIG. 1 is a schematic diagram illustrating a system architecture chart for an embodiment herein.

FIG. 1 is a schematic diagram illustrating a broader decision-making context in a system architecture chart of an embodiment herein. The decision-maker 108 may enter information through a range of devices including mobile phones, tablets, computers, appliances, etc. This information can be input through a variety of modalities including spoken, typed, constructed through a series of GUI interactions, etc. The information can be either problem case information or a query. The query can be in the form of a natural language, structured language, or any other query format. The problem case information that the system uses can be multimodal and can take the form of text, images, audio, or any other media form.

In general, the embodiments herein are intended to allow interaction to occur over a period of time and to support an iterative refinement approach. Therefore, one aspect of embodiments herein is a repository of all relevant analysis and decisions made to date. This repository 106 contains a representation of the reasoning and decision process not only as an efficiency mechanism, but allows the system to re-evaluate assumptions and decisions in light of new evidence relevant to the case. This allows users to interact with this representation, accepting, rejecting, or modifying it to as they think necessary to explore alternative solutions based on the users' insights into the validity or importance of the evidence or reasoning chain. This repository 106 is not only useful in the current evolving decision making interaction, but can be used to track the provenance of decisions that were made in the past and allow notification of actions to take based on newly arriving information that comes possibly years after decisions were made. For example, if a new study reports a contraindication for a drug in a given situation, the system could use this repository 106 of prior analysis to reevaluate its conclusions and provide relevant notification of alternative therapies to a patient that has been on this drug for years.

Lastly, in general, all embodiments herein are meant to inform the decision making process and allow the decision-maker 108 to view alternatives and associated confidences in proposed answers, explore the evidence and reasoning process the system used to come to its conclusions, and to get feedback on what additional information, if provided, would result in changing the answers.

The term diagnosis used in the medical domain can be generalized to mean "inform" in other domains. The medical examples found herein illustrates this through answers, confidences, dimensions of evidence, associated evidence passages, and documents where this evidence is found, as well as, reliability of the evidence source. In the medical domain, the embodiments herein can be used as a clinical decision support tool by physicians who are providing care to a patient. Examples of queries include (but are not limited to): what clinical conditions are characterized by a set of symptoms?; what is the "differential diagnosis" (a ranked list of diseases) that could potentially cause a set of symptoms, conditions, findings? (this can be conditioned by providing other pertinent patient information such as active diseases, current medications, allergies, past disease history, family disease history and patient demographics); what tests would increase or decrease confidence in a given disease hypothesis present in the differential diagnosis?; and/or what treatments are recommended for a specified disease, given information about the patient?; etc. In the medical domain, the problem case information can be electronic medical records.

The question-answering system derives answers from a repository of 'domain knowledge'. The embodiments herein leave delineation of the domain knowledge up to the question-answering system. The question-answering system in the exemplary medical implementation actually uses the natural language of medical text books, clinical guidelines, and other documents as the domain knowledge as well as structured sources of information provided in databases or ontologies or any other potential structured form.

In general, the embodiments herein describe a decision-support application 104 that is positioned in-between a source of problem case information 102 and a question-answering system 110 using the example of a medical diagnosis system. However, as would be understood by those ordinarily skilled in the art, the embodiments herein are not limited to medical diagnosis systems. To the contrary, the embodiments herein apply to diagnostic problem solving in any other complex-system domains that require question answering over unstructured material. Examples of such domains include aircraft maintenance (and other vehicles of similar complexity) and information technology support (call centers). This system could be used for automobiles, submarines, or even less complex but likely more universally accessible applications, for example, finding answers to "how to" queries in information technology or suitable meal recipes given input specifications such as ingredients, cost requirements, time, complexity, elegance, etc. These are all characterized by large amounts of structured and unstructured "problem case information" and domain knowledge, and requiring a deep question-answer type technology. Therefore, while the examples herein utilize a medical diagnosis system, those ordinarily skilled in the art would understand that the embodiments herein are applicable to all question-answer systems and the embodiments herein are not limited to just the exemplary medical diagnosis system that is used as a platform to illustrate the embodiments herein.

The system 104 comprises software modules (embodied on a computer readable medium) including an input/output module, a problem case analysis module, a question generation module, a hypotheses and evidence module, etc. The QA system 110 includes a question-answering module, etc. The objective of decision-making is to diagnose and solve problems that arise in a complex system 100 specified in the domain. A human expert (user) 108 who interacts with the decision-support application 104 (through items 100 and 102) makes decisions. A record of past decisions and the associated information used to arrive at the decision is maintained in the repository 106. In some embodiments, the question-answering module can match the query to at least one of the previously generated medical diagnosis queries that were generated by the question generation module and stored in the repository 106.

The decision-support application 104 may be triggered in several ways. In one mode, the decision-maker 108 asks a query about a particular case. The application 104 may expand the query with relevant problem case information and submit it to the question-answering (QA) system 110. The resulting answers or hypotheses are then presented to the decision-maker 108 who may iterate further, honing in to an acceptable resolution of the problem.

Another mode of operation assumes the existence of standing queries defined by the question generation module and/or the decision-maker 108. As new case information comes in, these queries are automatically run by the decision-support application 104 without the active involvement of the decision-maker 108. The results may be proactively sent to the decision-maker 108 or stored in the repository 106 for a subsequent scheduled interaction.

The above modes of operation assume the presence of active problem cases that are yet to be satisfactorily resolved. Another mode of operation can be triggered by changes in the content of domain knowledge used by the question-answering system in item 112. In the medical domain, new clinical literature and guidelines are continuously being published, describing new screening procedures, therapies, and treatment complications. The decision-support application 104 can use its repository 106 of past analyses and decisions to determine if any of its previous cases would be sufficiently affected by this new knowledge, and if so, send alerts to the responsible decision-makers 108.

Thus, FIG. 1 can also be considered to illustrate an exemplary system embodiment herein that comprises a first repository 102 maintaining problem case information, a computer processor 104/110 (running the modules) operatively connected to the first repository 102, and a second repository 106 operatively connected to the computer processor 104/110. Items are considered operatively connected to each other when the items are directly or indirectly connected to one another (e.g., physically, functionally, wired, wirelessly, etc.).

This "computer processor" 104/110 automatically analyzes the problem case information in order to identify semantic concepts, relations, and data and automatically generates at least one diagnosis query from the semantic concepts, relations and data. The computer processor 104/110 also automatically generates a plurality of diagnosis answers for each diagnosis query, and calculates confidence values for each of the answers based on numerical values for several dimensions of evidence that are relevant to the problem-solving domain. The computer processor 104/110 can then automatically calculate corresponding confidence values for each of the diagnosis answers based on the numerical value of each evidence dimension of evidence sources of the confidence values. Further, the computer processor 104/110 can then automatically generate links to each item of evidence to allow the user to examine the passages that justify the answer in a given. For example, links can be generated to the source of a passage, its type (text book, guideline, journal article, web content, database or structured source). The computer processor 104/110 also outputs the queries, the answers, the corresponding confidence values, the links to the evidence sources, and the numerical value of each evidence dimension to the decision-maker 108 and/or the second repository 106.

Figure 2:
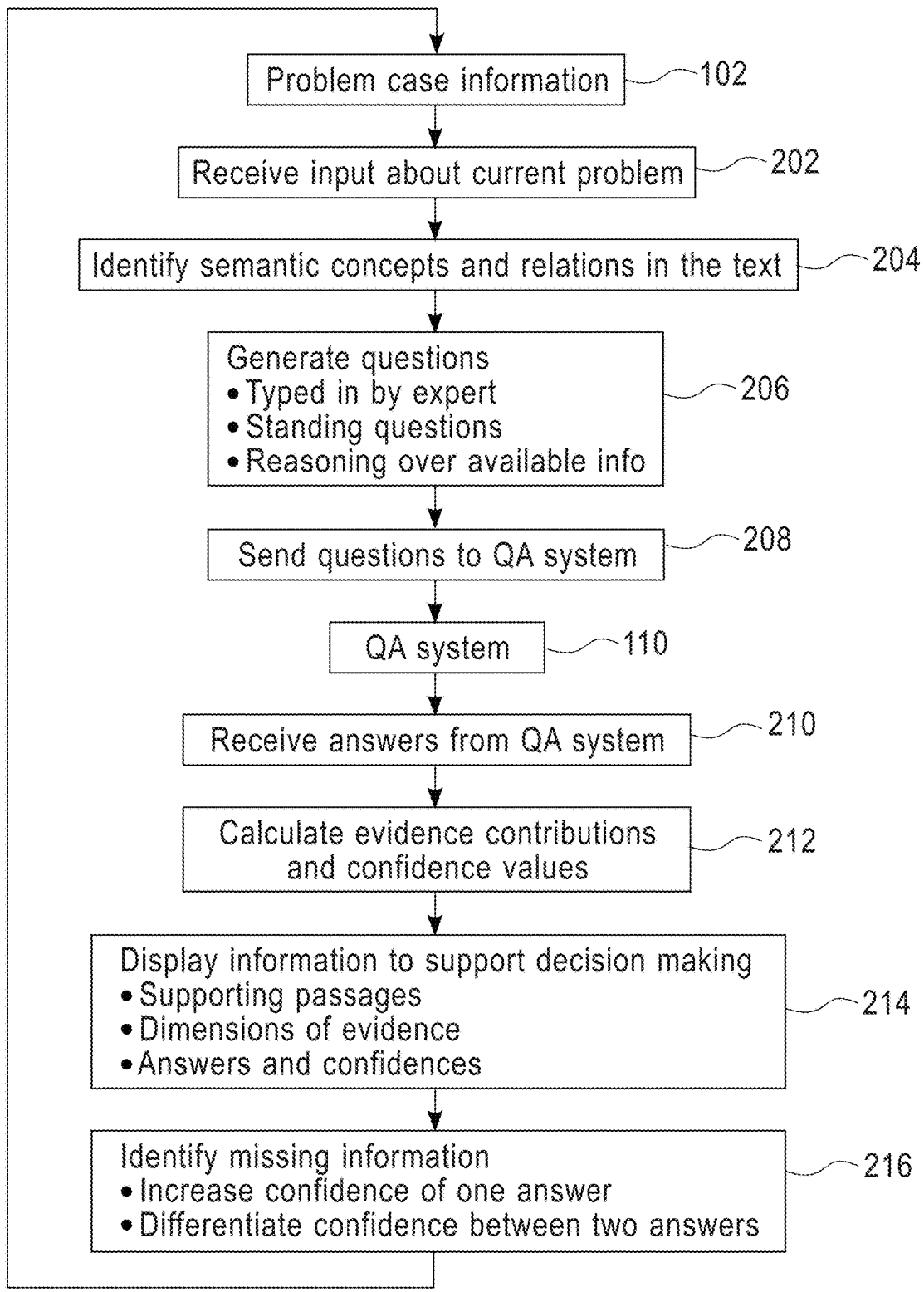
FIG. 2 is a schematic diagram illustrating of the decision support process flow.

FIG. 2 is a schematic diagram illustrating the decision support process flow performed by the decision support application 104. More specifically, FIG. 2 illustrates the flow of information from the problem case information 102 to the question-answering system 110 and the flow of information returned from the question-answering system 110 back to the decision-maker 108. Thus, the method receives problem case information using the input/output module. Further, in the medical domain, the problem case information can comprise illness symptoms of a patient, family history of the patient, demographics of the patient, etc. The output from the question-answering system 110 is used by the decision-maker 108 to either make a decision or seek additional information about the problem.

In item 202, the method receives input about the current problem. The method can receive a user inquiry through the input/output module in the form of a free-form query, a free-form statement, and/or keyword search, etc. The input from the problem can be multi-modal, such as text, audio, images, and video. The text can be unstructured, such as paragraphs of problem description in natural language, or structured, such as the content derived from a database. For example, in the medical domain, the input can be clinical information pertinent to a patient's "History of Present Illness" (HPI). This can be in the form of paragraphs of unstructured text describing any aspect of the patient's HPI as written or dictated by a nurse or physician, or semi-structured, with shorter sentences or snippets assigned to specific HPI categories.

The input information can come in over time. The input may be triggered by a change in the problem condition, the result of additional tests or procedures performed, or a response to a query for more information generated by the decision-maker 108. In addition, the information within the domain knowledge content 102 can change according to evolving demographic changes, evolving medical discoveries, evolving medication conflicts, evolving side effect information, etc. This time-stamped information is recorded in the repository 106 in the system.

In item 204, the method automatically analyzes the problem case information 102, using the problem case analysis module, in order to identify semantic concepts, relations and other relevant knowledge (e.g., medical patient data). Thus, the method identifies semantic concepts, relations and other relevant knowledge when the incoming information is unstructured, such as natural language text, audio or images, the concepts, relations and other kinds of information relevant to the domain has to be identified. This is done by software components called "annotators". They can be procedural code, rule based, using programmed logic or in many other forms for determining concepts, relations and other relevant information. They could, for example, be based on machine learning, using a set of training data containing known concepts and relations.

Figure 3:
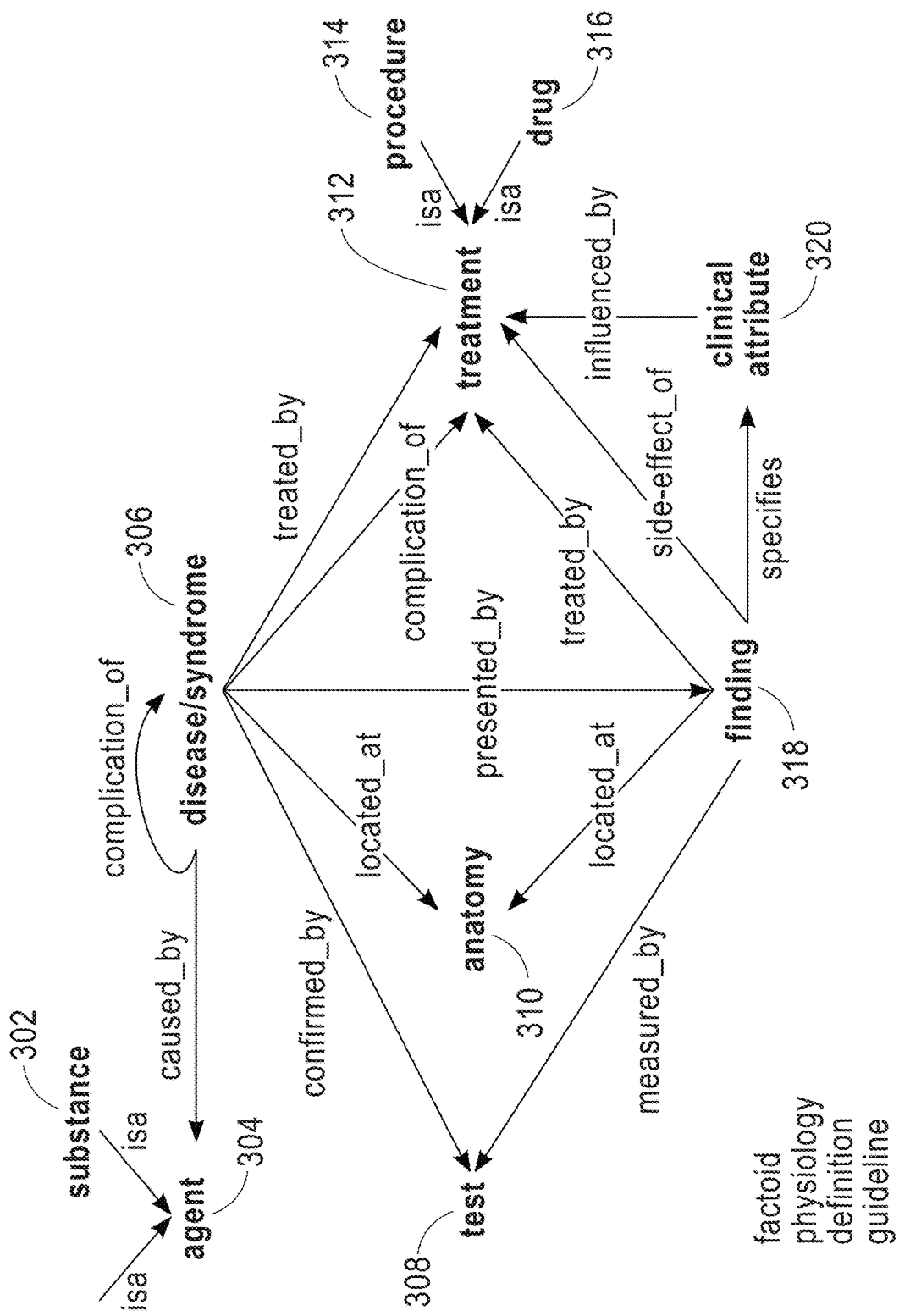
FIG. 3 is a schematic diagram illustrating a semantic model for the medical domain.

For the medical domain, annotators can recognize the phrases relating to clinical concepts such as patient symptoms, current medical conditions, clinical findings, medications, family history, demographics, etc. Annotators may also identify relations between entities such as location of symptom, the severity of a condition, or the numerical value of a finding. The concepts and relations are represented by domain-specific semantic model or type system. An example of such a semantic model for the medical domain is shown in FIG. 3. More specifically, in the example shown in FIG. 3, various elements have different logical/causal relationships. For example, substance 302 has an "is a" relationship to agent 304 indicating that substance 302 "is an" agent 304. Similarly, a disease/syndrome 306 can be caused by the agent 304, and the disease/syndrome can be a complication of another disease/syndrome in item 306.

With respect to the disease/syndrome 306, it can be confirmed by test 308, may be located at anatomy location 310, can be presented by a finding 318, and can be a complication of a certain treatment 312 (or may be treated by the treatment 312). The treatments 312 may be a procedure 314, a drug 316, etc. Similarly, with respect to the finding 318, it may be measured by the test 308, located at the anatomy location 310, treated by the treatment 312, be a side effect of the treatment 312, or may specify a clinical attribute 320. Additionally, the clinical attribute 320 may be influenced by the treatment 312. Therefore, the semantic model illustrated in FIG. 3 (which may be referred to as a factoid physiology definition guideline) illustrates various concepts and relations of a domain-specific semantic model.

In item 206, the method can receive queries or automatically generate queries from the semantic concepts, relations and data using the question generation module. Thus, using the semantic concepts and relations found in the previous step, queries for the question-answering system can be automatically formulated. Alternatively, it is also possible for the decision-maker 108 to enter queries in natural language or other ways, as described above.

In case of automatic formulation, a set of "standing" queries can be designed as a template. For example, a standing query in the medical domain is the "differential diagnosis." This is a list of potential hypotheses of the diseases or other medical conditions that explain a patient's symptoms and abnormal findings. The diagnosis query templates herein have blank slots for concepts such as symptoms, findings, past diseases, current medications, allergies, etc. Once the semantic concepts and relations are identified, these fill in the blanks in the template, resulting in a synthesized query. The concept of a template is a general computational element for automatically constructing a set of relevant queries (queries) to the underlying question-answering system that is used to synthesize and return information relevant to the specific information need at hand.

There are many ways to implement templates. For example, queries may be automatically generated in item 206 based on what is known and unknown about the problem case. For example, in the medical domain, if symptom and finding concepts have been identified in the patient case information, but no diseases are found, a diagnosis query may be generated. The physician is also able to type in a query such as "What is the diagnosis?" and rely on the rest of the context to come from the semantic concepts. The physician is also able to fine-tune the querying by specifying more constraints such as "Is there an infectious cause of these symptoms?"

In item 208, the method sends queries to the QA system 110. Thus, the method can automatically generate a plurality of answers for each query using the question-answering module. Once a query is formulated, the question-answering system 110 is invoked. For aiding the subsequent interpretation of the answers, a query may be converted into multiple queries. Each query in this set may contain a subset of the concepts found about the problem. For example, a clinical diagnosis query containing symptoms, findings, family history and demographic information, could generate a series of queries as follows, where the text in the < > characters is replaced by the corresponding concepts found in the case text: "What disease of condition could cause <symptom>?"; "What disease of condition could cause <symptom> and <findings>?; "What disease of condition could cause <symptom>, <findings> and <family history>?; "What disease of condition could cause <symptom>, <findings>, <family history> and <demographics>?; etc. This build-up of information in the query makes it possible to calculate the marginal contribution of findings, family history and demographic information to the confidence of a diagnosis. Other strategies for breaking down a query into a set of queries could also be used.

The method receives answers from the question-answering system in item 210. For each query submitted, the question-answering system 110 returns a list of answers, their confidences, evidence dimensions, and evidence sources. The confidence of each answer can, for example, be a number between 0 and 1. This confidence is constructed from various answer scorers in the question-answering system, which evaluates the correctness of the answer according to various dimensions of evidence sources. For example, a candidate answer to a medical diagnosis query can be evaluated in terms of the semantic type of the answer. The score along this dimension will be high if the answer is a type of disease or medical condition that can be considered as a diagnosis. For every answer to a query, the passages of domain knowledge from which the answer was extracted are also available from the question-answering system. This can be snippets of text that match the structure of the query or entire documents that were returned from search components during the question-answering process. For each passage, a citation to the original source of information is also recorded.

In item 212, the method further automatically calculates confidence values for each of the answers based on numerical values for several dimensions of evidence that are relevant to the problem-solving domain. The numerical value of each evidence dimension can be based upon the various semantic concepts and relations found in the problem case information 102, as described by the method in item 204. For example, in the medical domain, these could be the patient's symptoms, findings, family history, demographics, etc.

The above processes described methods of formulating multiple queries containing a subset of the concepts found in the problem text. By analyzing answers and their confidences for these queries, an estimate of the marginal contribution of these concepts can be generated. For the example for the queries generated, the marginal impact of symptoms, findings, family history and demographics are calculated. Other techniques for achieving this are possible as well.

In item 214, the method displays information to support decision-making. The list of answers is displayed along with answer confidences for the decision-maker 108 to evaluate (see FIG. 4 for an example). Thus, the method outputs the queries, the answers, the corresponding confidence values, the links to the evidence sources, and the numerical value of each evidence dimension using the input/output module upon user inquiry. Additionally, the decision maker can explore each evidence dimension further by viewing each piece of evidence and explore its associated provenance. For example, a piece of evidence may be a supporting passage, reasoning chain, or database fact. Similarly, examples of associated provenances include journal articles, textbooks, and databases. Further, when outputting the numerical value of each evidence dimension, this embodiment can illustrate the amount each evidence dimension contributes to a corresponding confidence value (on a scale or percentage basis, for example) and illustrate how changes in each of the numerical value of each evidence dimension produce changes in the corresponding confidence value.

Further, the embodiments herein automatically and continuously update the diagnosis answers, the corresponding confidence values, and the numerical value of each evidence dimension based on revisions to the problem case information to produce revised queries, answers, corresponding confidence values, etc. (using the question-answering module). This method can also automatically output the revised queries, answers, and/or corresponding confidence values when a difference threshold is exceeded. This "difference threshold" can comprise a time period (e.g., hours, weeks, months, etc.), the amount one or more answers change (e.g., percentage change, polarity (yes/no) change, number of answers changing, etc.) and/or an amount of confidence value changes (percent confidence change, confidence polarity change, etc.).

Therefore, the decision support application 104 continuously and dynamically automatically provides queries and answers based upon the evolving semantic concepts, relations and other relevant data (e.g., medical patient data) in order to provide the highest confidence answers and the most information on such answers to the decision-maker 108. Rather than providing static applications that always provide the same answers when given the same input (as is done conventionally), the embodiments herein continually update the values and relationships of the numerical values of each evidence dimension to change the confidence values of potential answers. When the confidence values of the potential answers change, the answers that are most highly recommended can also change, thereby dynamically allowing the decision-maker to be provided with different best answers as the problem case information evolves over time.

Thus, the embodiments herein provide substantial advantages over systems that generate answers and confidence values based on preset, fixed criteria that is rarely revised (or only revised at periodic updates (e.g., software updates)). For example, in the medical domain, by acting dynamically, previous answers and recommendations can change based on evolving demographic changes, evolving medical discoveries, evolving medication conflicts, evolving side effect information, etc., within the domain knowledge content 112. Therefore, the embodiments herein can change a course of medical treatment advice for a patient, even if that patient does not experience a personal change, merely because other data within the domain knowledge content 112 evolves over time. This allows medical providers a fully automated system for constantly prescribing the best medical treatment for their patients as medical advances and demographics change over time.

Figure 4:
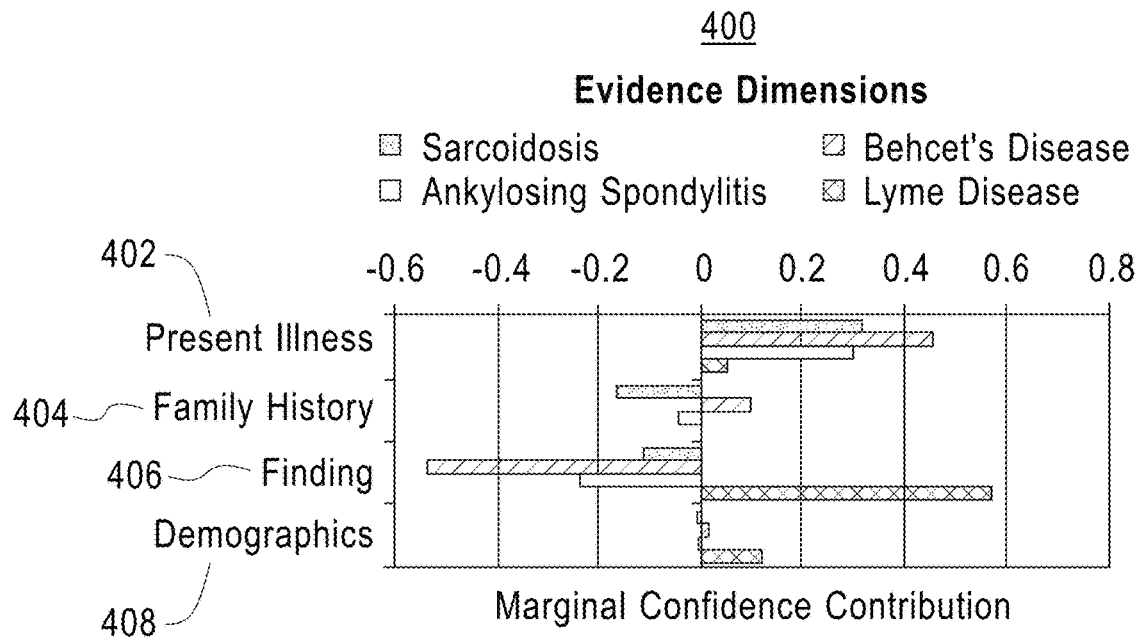
FIG. 4 is a schematic diagram illustrating the marginal contribution of evidence along the dimensions of present illness, family history, findings, and demographics for four disease answers.

In many domains, the answer with the highest confidence need not be the appropriate answer because there can be several possible explanations for a problem. For example, in the medical domain, several diseases may cause a patient to present a set of symptoms. In addition to displaying a list of answers and their confidences, one or more of the answers may be selected to drill down into the dimensions of evidence. FIG. 4 is a schematic diagram illustrating the contribution of each dimension value of evidence from evidence sources to the overall confidence of an answer. The output shown in FIG. 4 compares each dimension across multiple answers. FIG. 4 illustrates the marginal contribution of evidence 400 along the dimensions of present illness 402, family history 404, findings 406, and demographics 408 for four disease answers. In this example, the "dimensions" are 'present illness', 'findings', 'family history', and 'demographics' and each has its own value. This comparative analysis of multiple answers along the evidence dimensions allows the decision-maker 108 to consider and visualize the trade-offs in evidence in order to arrive at a decision.

The decision-maker 108 can also drill down deeper into each answer and dimension of evidence and examine the supporting pieces of evidence that justify the answer along that dimension. For example, the source of the passage, its type (text book, guideline, journal article, web content) and a link to the source is provided for the decision maker to delve deeper and confirm its validity.

The method can also identify missing information in item 216. More specifically, this embodiment automatically identifies information relevant to the answers that is not contained within the problem case information as missing information, and further automatically identifies the amount the missing information affects the corresponding confidence values (both using the using the question-answering module) and outputs this information to the user.

If the answers and their evidence returned by the question-answering system are not adequate for arriving at a decision, the application 104 may be used to identify missing information that has potential for affecting the confidence in answers. For a given answer, the decision-maker 108 may want to know what hypothetical information, if provided, can produce the greatest change in the confidence. For example, in the medical domain, if the answer is a disease, the missing information may be a lab test that confirms or rules out the disease. It may also be other signs or symptoms not specified for the patient. In reality, there may be a large amount of missing information associated with an answer and the embodiments herein can rank the missing information. Characteristics that can be used to rank the potential value of the missing information are factors such as the cost of obtaining this information, the time taken, and the amount by which the missing information affects the confidence of the answer.

When two answers have similar confidences, making it difficult to choose between them, it is helpful to identify the missing information that will cause the biggest difference between these confidences. For example, in the medical domain, the answers may be two related diseases and the missing information may be a lab test designed to differentiate between them. This evidence could increase as well as decrease the confidence of one answer thus helping to ascertain the correct diagnosis in the case of a medical diagnostic system.

The identification of missing information need not only be done at the initiative of the decision-maker 108. When certain criteria are met, for example, confidence of two top answers are very close, the application 104 itself may take the initiative and may automatically request the missing information.

Once the missing information is identified, the decision-maker 108 has to seek this missing information using procedures specific to the domain. In the medical domain, this may require ordering lab tests or asking the patient for more information. When this missing information becomes available, it is sent back to the decision-support as described above and a new iteration of question-answering and decision support process illustrated in FIG. 2 is begun.

Figure 5:
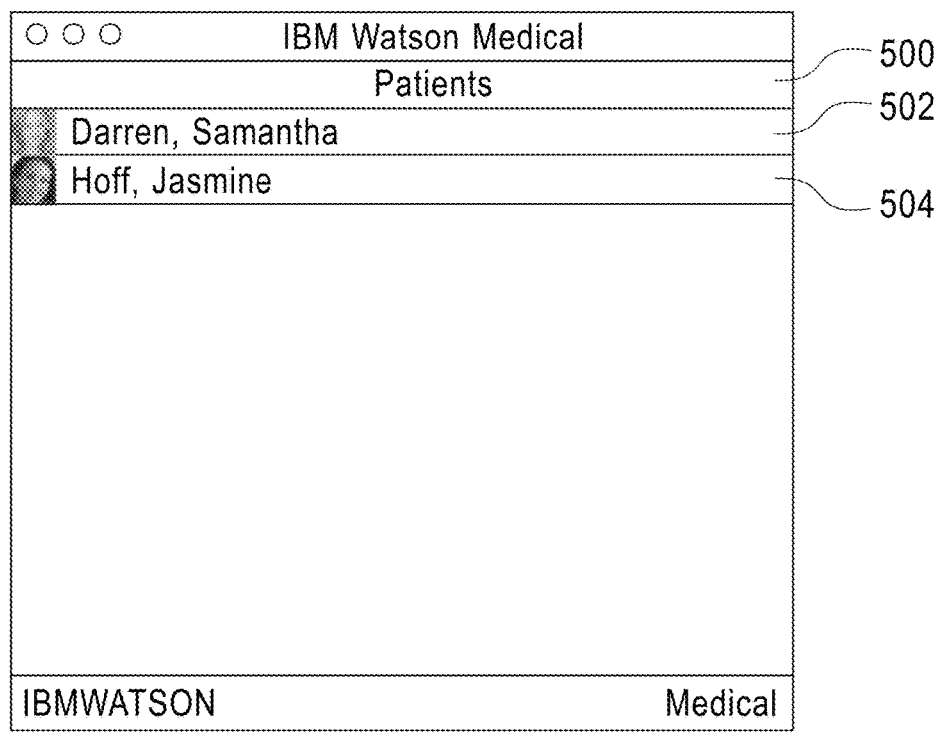
FIG. 5 is a schematic diagram illustrating an embodiment herein applied to the medical domain.
Figure 6:
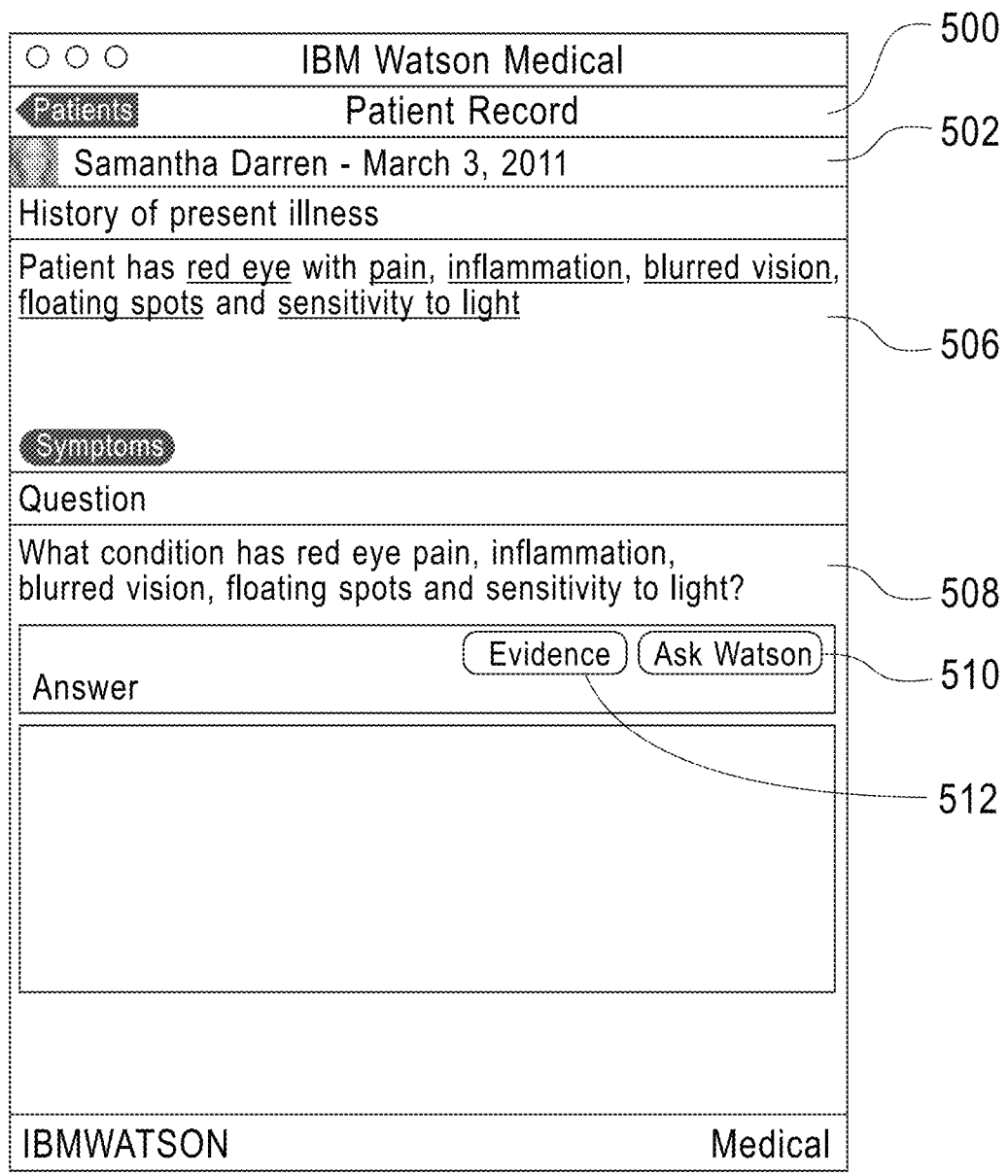
FIG. 6 is a schematic diagram illustrating an embodiment herein applied to the medical domain.

FIGS. 5-14 are schematic diagrams of screenshots that can be presented to the users. In FIG. 5, profiles 502, 504 for two patients are shown on a screenshot 500. Additional profiles for further patients can be created. In FIG. 6, the first patient 502 has been selected and has described symptoms that are listed in the History of Present Illness section 506. This information can be input by a health care professional into an Electronic Health Record (EHR) or merely made available for the system to consider by typing into the box 506. The proposed system can pull the relevant information automatically from the health record or text field above, use analytics to find relevant concepts, classify them as belonging to the symptoms dimension and automatically generate the query listed in the queries field 508. Alternatively, the user (physician/patient) could enter a query directly into the query field. The user can then click on the "Ask Watson" button 510 to proceed. FIG. 6 also lists an "Evidence" button 512, which is discussed below.

Figure 7:
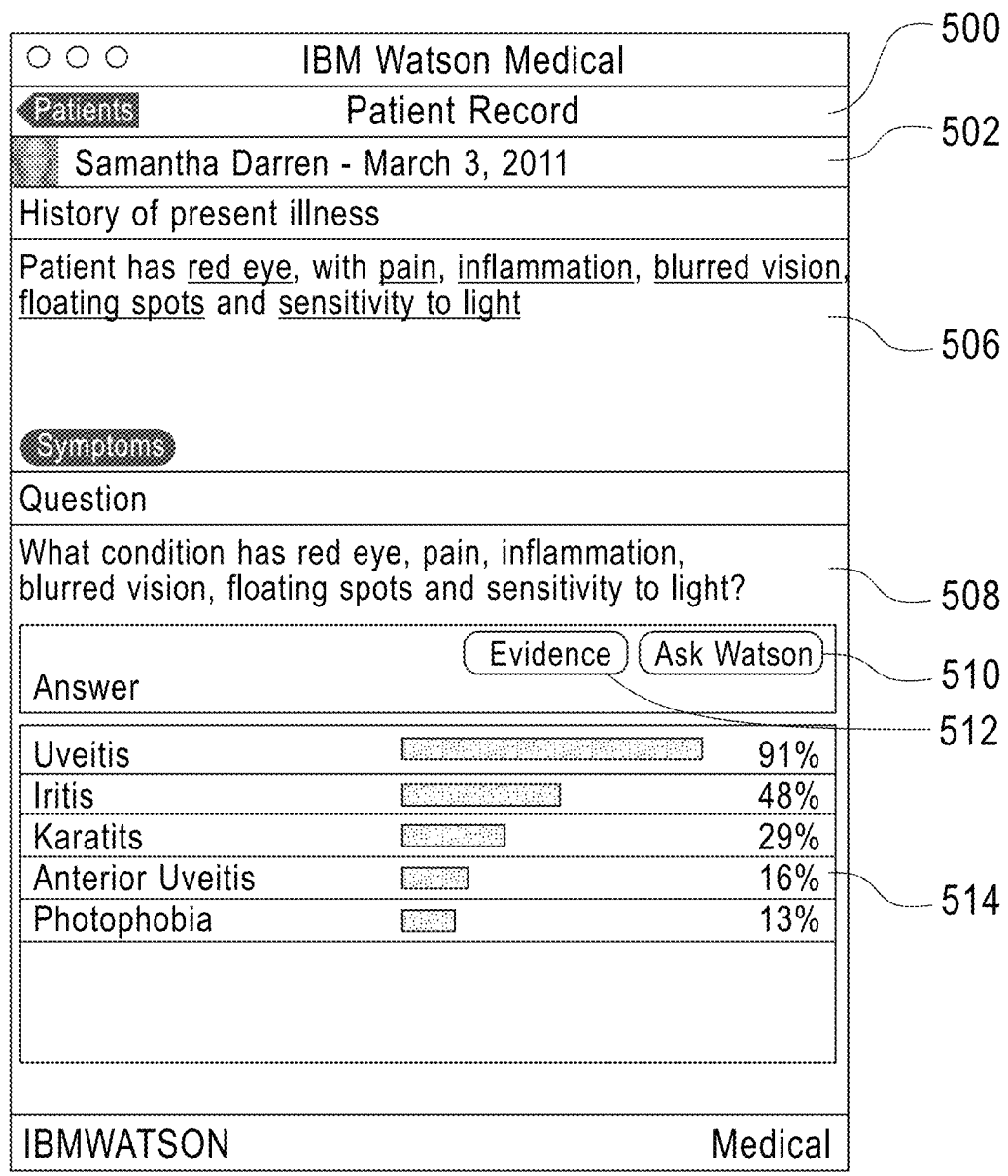
FIG. 7 is a schematic diagram illustrating an embodiment herein applied to the medical domain.
Figure 8:
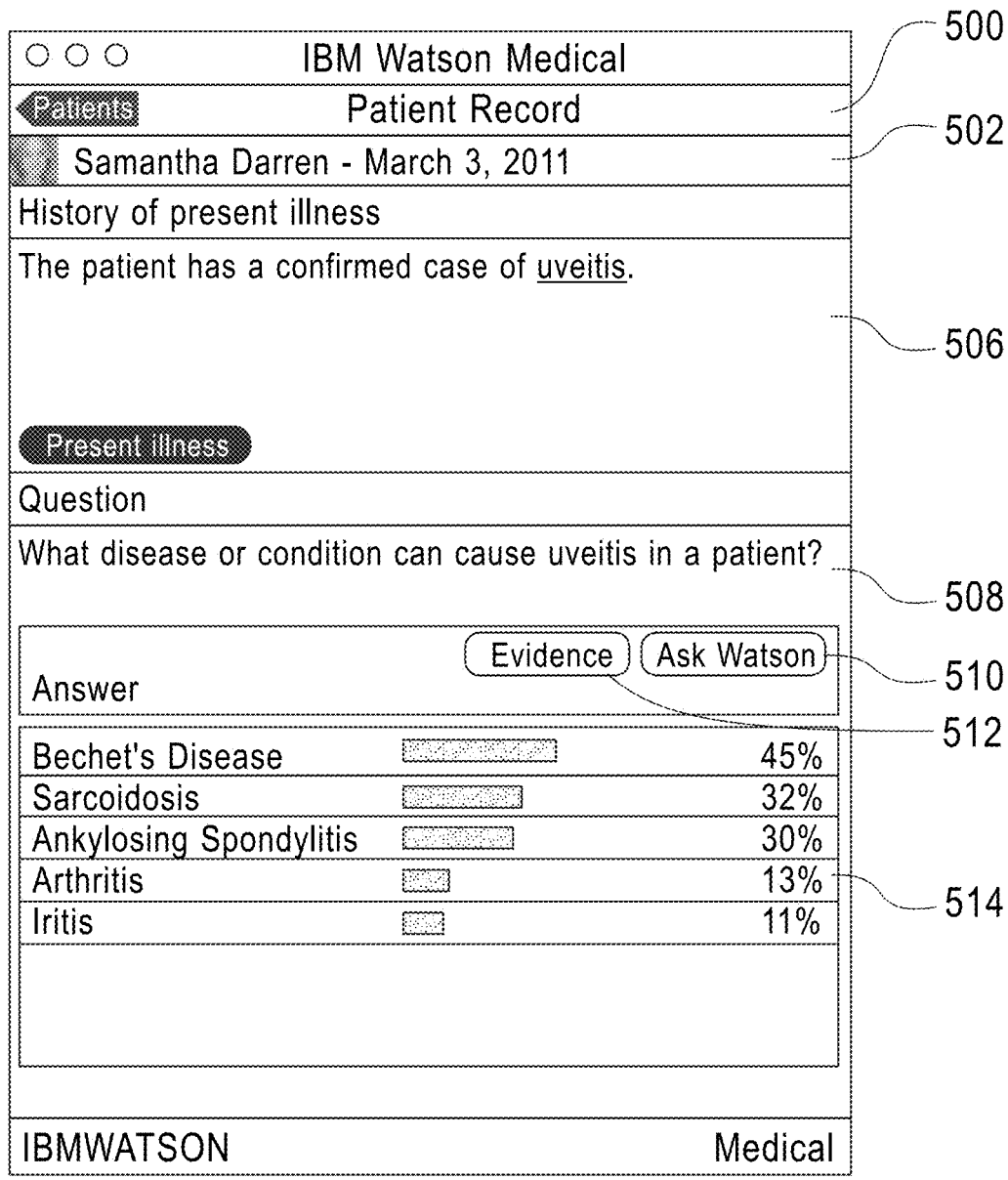
FIG. 8 is a schematic diagram illustrating an embodiment herein applied to the medical domain.

In FIG. 7, the decision-support application 104 has generated a set of possible answers to the query with associated confidence scores associated with each answer and the same is displayed in area 514. In FIG. 8, having confirmed the condition, the user can enter the condition into the History of Present Illness section, or the condition can be extracted automatically from the EHR. Subsequently, the physician can ask another query or have the decision-support application 104 automatically generate another query.

Figure 11:
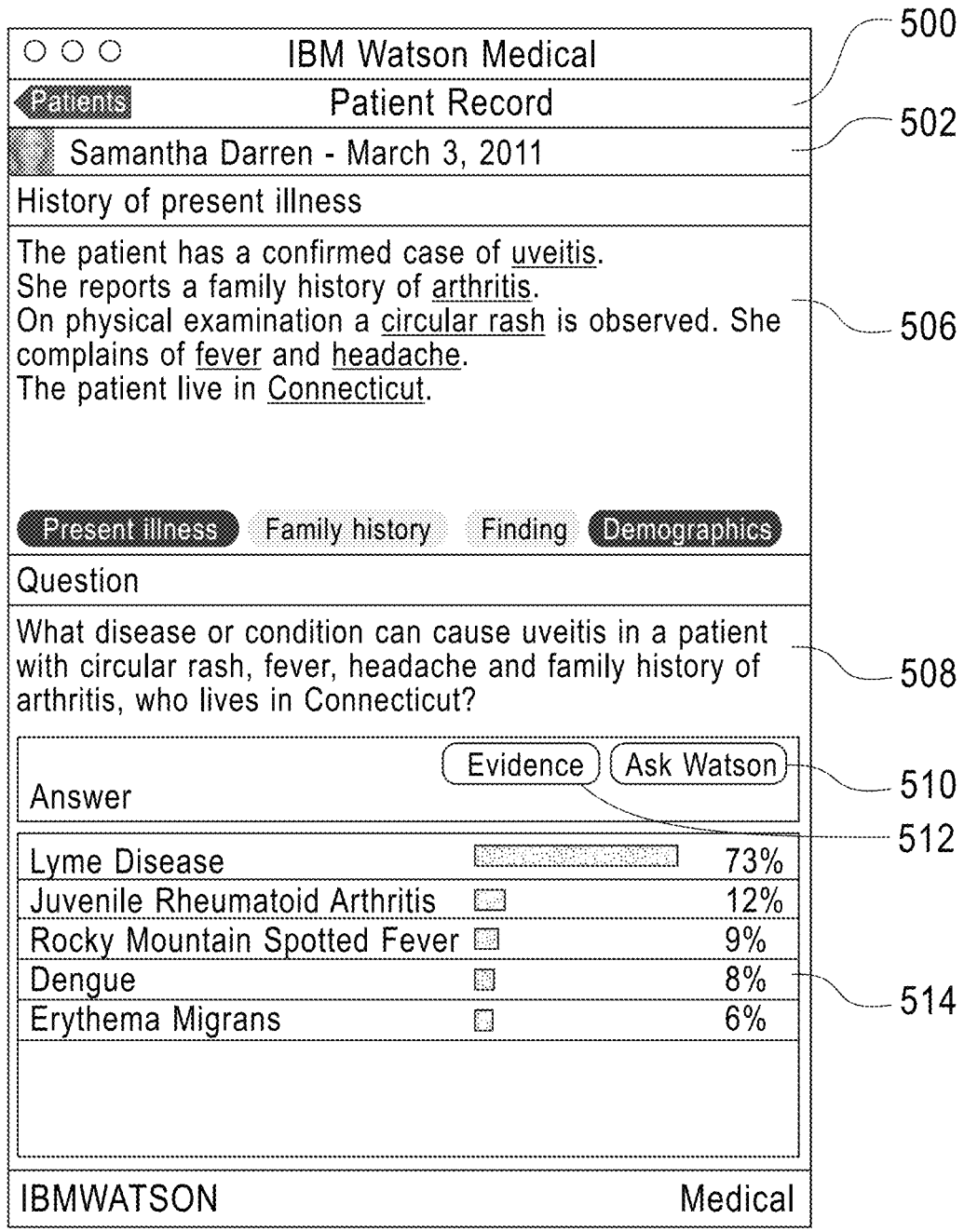
FIG. 11 is a schematic diagram illustrating an embodiment herein applied to the medical domain.

In FIG. 9, the process continues with new information having been added in item 506 that is analyzed and grouped in relevant dimensions such as present illness, family history, etc. In FIG. 10, the same process continues as more information continues to be added in item 506, thereby refining the potential diagnosis. In FIG. 11, the process has reached a point where the decision-support application 104 indicates in item 514 with high confidence over other potential answers that the proper diagnosis for the particular patient is Lyme disease. From the example of FIG. 11, the information contained in these dimensions come from the case information (respectively, 'uveitis', 'circular rash . . . ', 'arthritis', and 'Connecticut'). The numerical value of each evidence dimension comes from the presence of the information contained in these dimensions in the medical content in the context of the hypothesized answer (e.g., Lyme disease).

Figure 12:
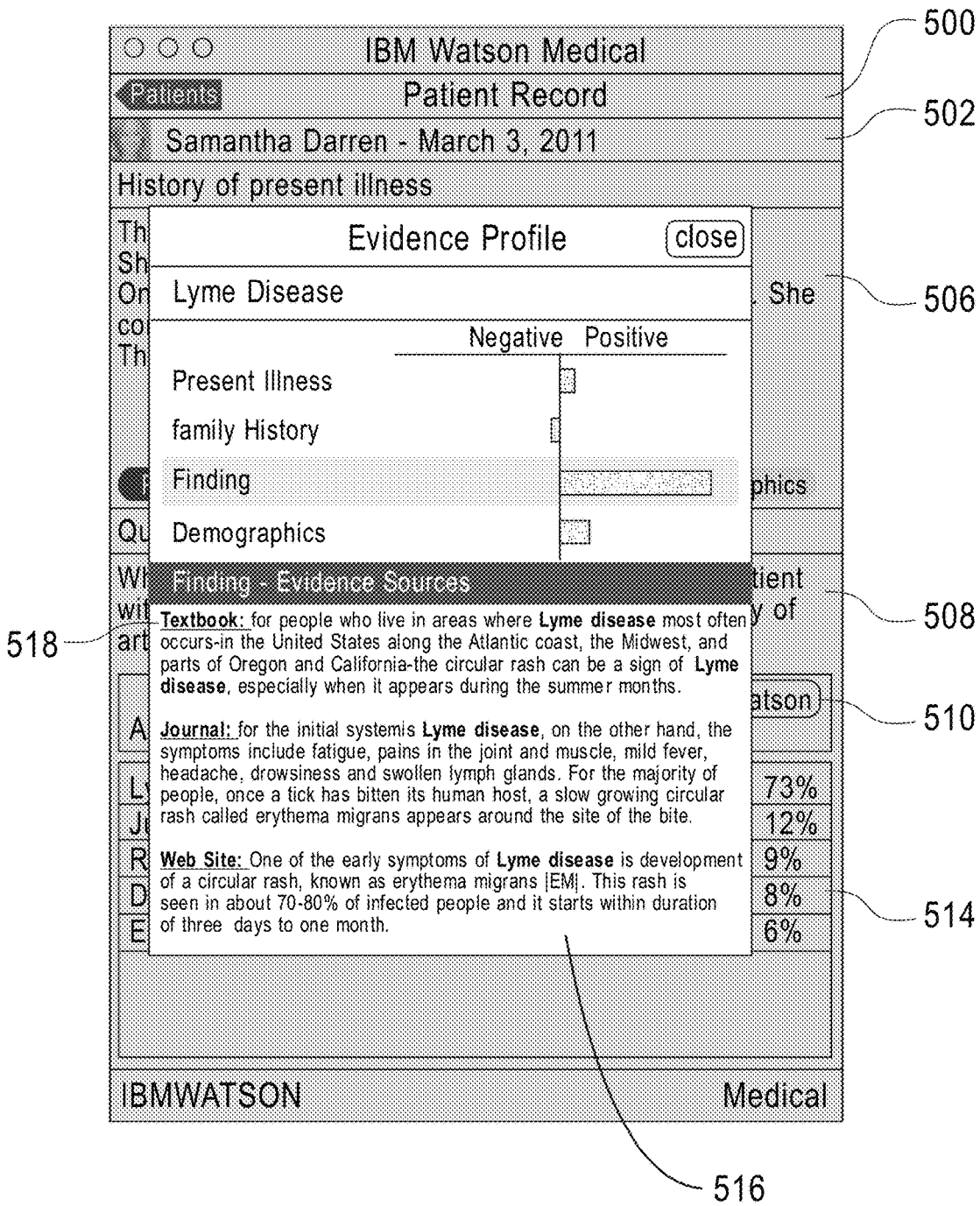
FIG. 12 is a schematic diagram illustrating an embodiment herein applied to the medical domain.
Figure 13:
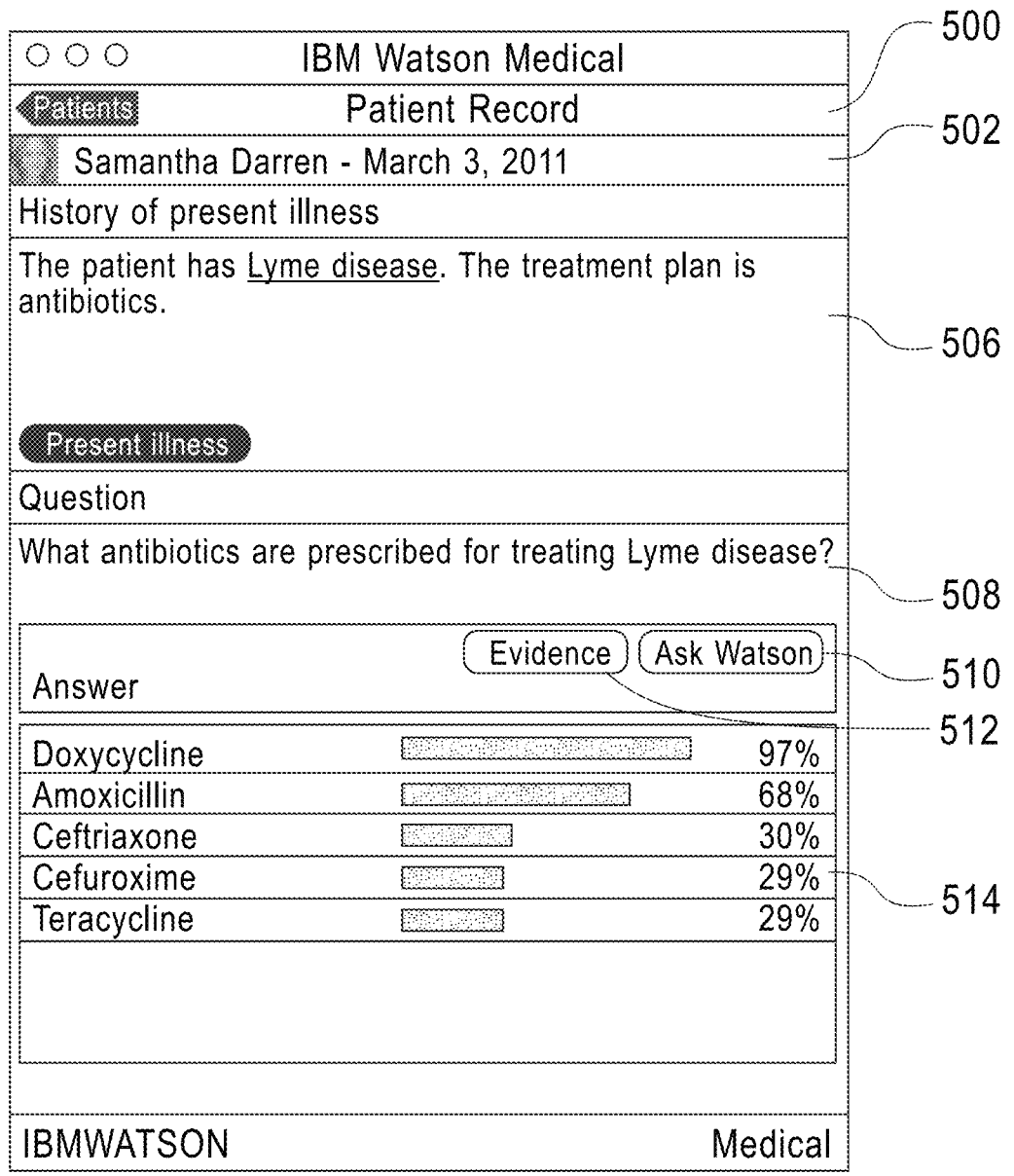
FIG. 13 is a schematic diagram illustrating an embodiment herein applied to the medical domain.
Figure 14:
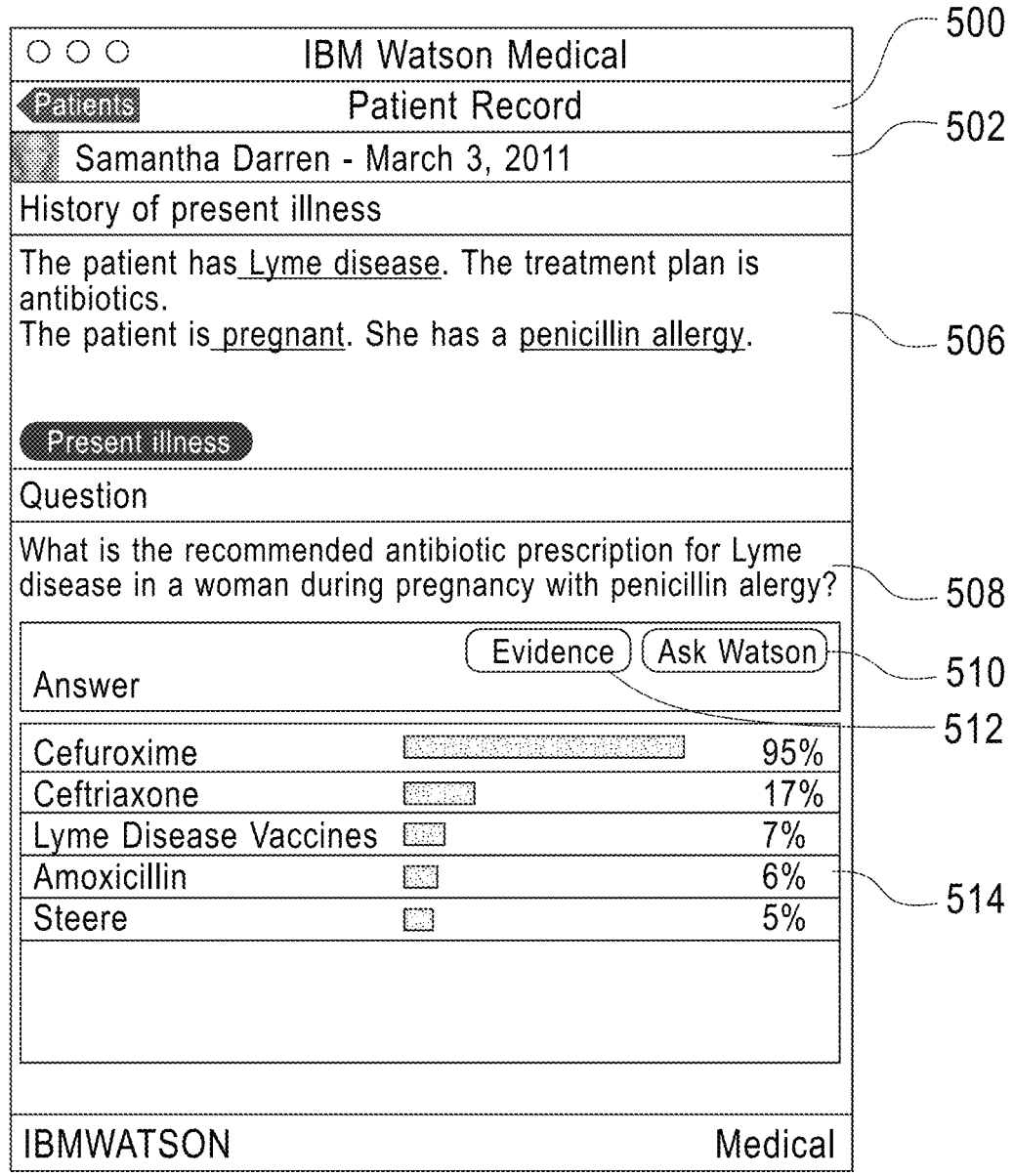
FIG. 14 is a schematic diagram illustrating an embodiment herein applied to the medical domain.

In FIG. 12, the decision-support application 104 allows the user to select the answer Lyme disease in order to view the evidence profile 516 for the answer. The application 104 reveals the dimensions of evidence and their associated contribution to the Lyme disease diagnosis. The user can then further select a particular dimension to explore snippets of evidence that contribute to this dimension. Finally, the application 104 allows for the physician to view the whole documents from which the snippets were derived by clicking on one of the links labeled 518 in FIG. 12, such as a textbook, journal, or website. In FIG. 13, the decision-support application 104 is again shown, except in this case the application 104 is directed towards exploring possible treatments for treating the identified condition. In FIG. 14, new information has been added or automatically extracted from the patient's medical record relevant to the appropriate treatment to the identified condition. In this case, the application 104 has identified that the patient is allergic to penicillin and that the patient is pregnant. The application 104 uses this information to find the appropriate treatment, in this case indicating a confidence score for a particular treatment option.

As will be appreciated by one skilled in the art, aspects of the embodiments herein may be embodied as a system, method or computer program product. Accordingly, aspects of the embodiments herein may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the embodiments herein may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the embodiments herein may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the embodiments herein are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments herein. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It is understood in advance that although this disclosure includes a detailed description on cloud computing, implementation of the teachings recited herein are not limited to a cloud computing environment. Rather, embodiments herein are capable of being implemented in conjunction with any other type of computing environment now known or later developed. Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service. Service Models are as follows: Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 15:
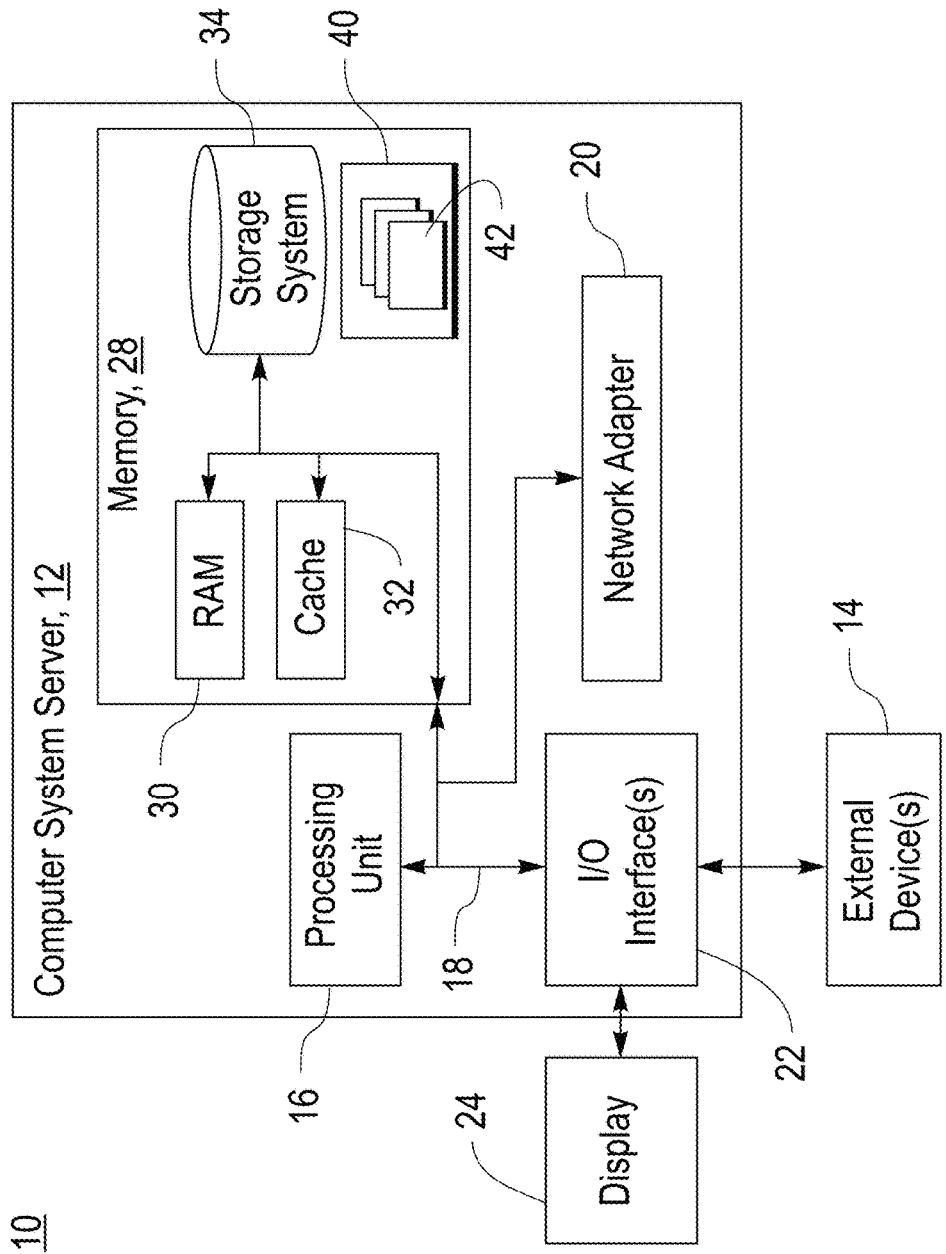
FIG. 15 is a schematic diagram illustrating a computing node according to an embodiment herein.

Referring now to FIG. 15, a schematic of an example of a cloud computing node is shown. Cloud computing node 10 is only one example of a suitable cloud computing node and is not intended to suggest any limitation as to the scope of use or functionality of embodiments of the invention described herein.

Regardless, cloud computing node 10 is capable of being implemented and/or performing any of the functionality set forth hereinabove. In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 15, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16. Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention. Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein. Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components can be used in conjunction with computer system/server 12. Examples, include, but are not limited to: microcode, device drivers, redundant processing units, external disk drive arrays, RAID systems, tape drives, and data archival storage systems, etc.

Figure 16:
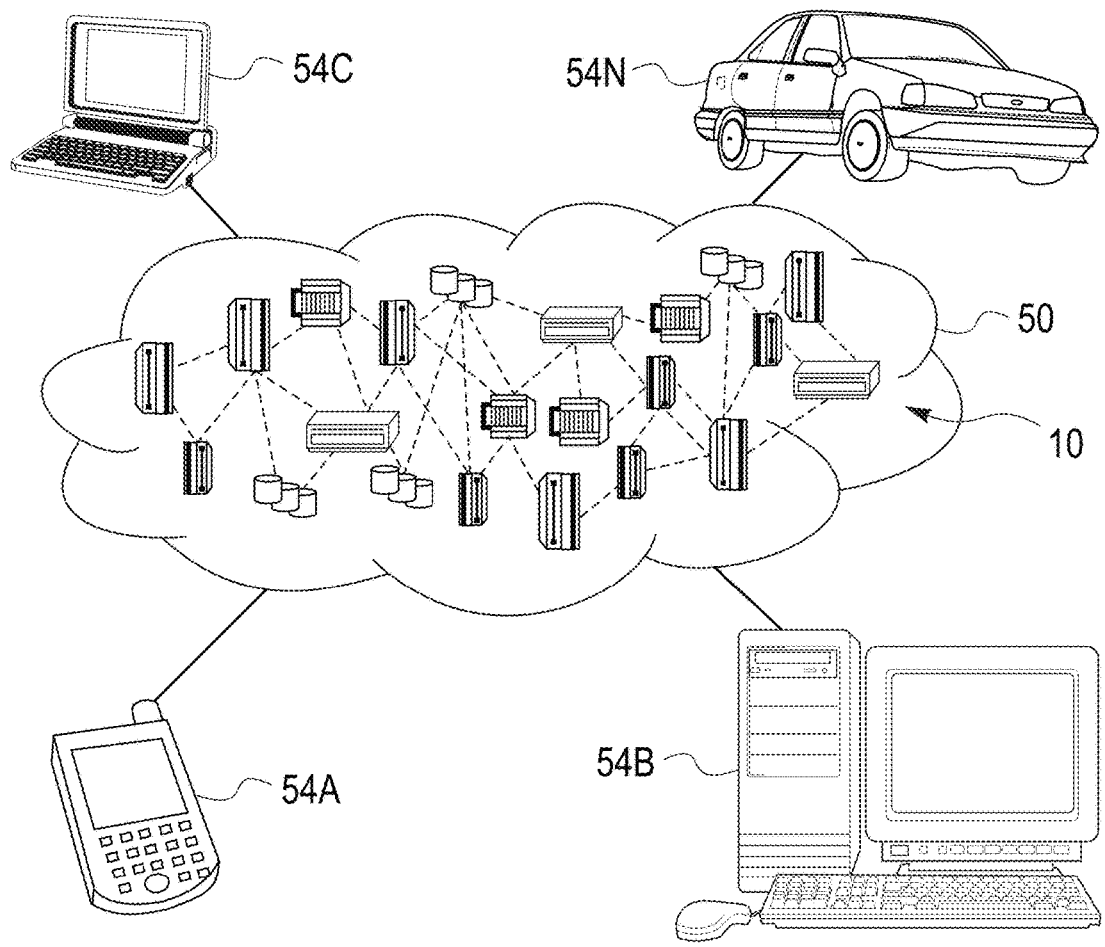
FIG. 16 is a schematic diagram illustrating a cloud computing environment according to an embodiment herein.

Referring now to FIG. 16, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Referring now to FIG. 17, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided: Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide). Virtualization layer 62 provides an abstraction layer from which the following examples of virtual entities may be provided: virtual servers; virtual storage; virtual networks, including virtual private networks; virtual applications and operating systems; and virtual clients. In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; transaction processing; and decision-support for problem solving using a question-answering system.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the embodiments herein has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
receiving, by a decision-support system for medical diagnosis and treatment, patient case information regarding a patient, said decision-support system comprising a computerized device that has access to evidence sources containing medical domain knowledge;
analyzing, by said decision-support system, said patient case information to identify semantic concepts by recognizing phrases in said patient case information logically related to medical concepts;
generating, by said decision-support system, a query by automatically supplying said semantic concepts to blank slots in a query template to generate said query, said query comprising a medical question;
generating, by said decision-support system, answers to said query by applying natural language processing techniques to match said query to passages of said medical domain knowledge within said evidence sources, said evidence sources comprising information in unstructured form;
calculating, by said decision-support system, numerical values of evidence dimensions for each of said answers by assigning different numerical values to each of said answers based on the correctness of each of said answers for different semantic concepts;
calculating, by said decision-support system, corresponding confidence values for said answers by combining said numerical values of said evidence dimensions as calculated for said answer;
outputting, concurrently by said decision-support system to a decision-maker for said patient, said answers, said numerical values of said evidence dimensions for each of said answers, said corresponding confidence values for said answers, and at least one automatically generated link to said evidence sources for each of said answers so that said answers, said numerical values of said evidence dimensions for each of said answers, said corresponding confidence values for said answers, and said evidence sources for each of said answers are usable by said decision-maker to make a decision regarding said patient;

storing, by said decision-support system in a tangible repository, said answers, said numerical values of said evidence dimensions for each of said answers, and said corresponding confidence values for said answers;

in response to new medical domain knowledge being added to said evidence sources, automatically repeating, by said decision-support system, said generating of said answers to said query, said calculating of said numerical values of said evidence dimensions for each of said answers and said calculating of said corresponding confidence values for said answers in order to determine whether previously generated answers and corresponding confidence values stored in said tangible repository would change based on said new medical domain knowledge; and, automatically sending, by said decision-support system, an alert to said decision-maker based on a change occurring in any of said previously generated answers and corresponding confidence values, said alert being usable by said decision-maker to re-evaluate said decision.

2. The method according to claim 1, further comprising automatically repeating, by said decision-support system, said generating of said query, said generating of said answers to said query, said calculating of said numerical values of said evidence dimensions for each of said answers, and said calculating of said corresponding confidence values for said answers based on new patient case information being received.

3. The method according to claim 2, further comprising automatically sending, by said decision-support system, an additional alert to said decision-maker based on any additional change occurring in any of said previously generated answers and corresponding confidence values based on said new patient case information being received.

4. The method according to claim 1, said generating of said answers being carried out by analyzing medical domain knowledge content.

5. The method according to claim 1, said generating of said query being carried out by receiving said query in a form of at least one of a free-form query, a free-form statement, and keyword search.

6. The method according to claim 5, further comprising receiving, by said decision-support system, an initial query from said decision-maker, said generating of said query comprising:

in response to said initial query, analyzing said patient case information, to identify said semantic concepts; and expanding said initial query using said semantic concepts to generate a specific natural language query.

7. The method according to claim 1, further comprising outputting, for a selected evidence dimension, each piece of evidence supporting said selected evidence dimension and an associated provenance for said piece of evidence.

8. The method according to claim 7, further comprising:

removing, by said decision-support system, a selected piece of evidence from said evidence sources contributing to a numerical value of an evidence dimension of a specific answer;

recalculating, by said decision-support system, said numerical value of said evidence dimension of said specific answer having said selected piece of evidence removed to produce a recalculated numerical value; and recalculating, by said decision-support system, a new confidence value of said specific answer based on said recalculated numerical value.

9. The method according to claim 1, further comprising:

identifying, by said decision-support system, information relevant to said answers that is not contained within said patient case information as missing information; and outputting, by said decision-support system, a request to said decision-maker to add said missing information to said patient case information.

10. The method according to claim 9, further comprising identifying, by said decision-support system, an amount said missing information affects corresponding confidence values of said answers.

11. The method according to claim 1, said alert being sent only when said change exceeds a difference threshold, said difference threshold being any of a percentage change in an answer, an answer polarity change, a percentage change in a confidence level and a confidence level polarity change.

12. A system comprising:

a first tangible repository maintaining patient case information regarding a patient; a computer processor operatively connected to said first tangible repository and having access to evidence sources containing medical domain knowledge; and a second tangible repository operatively connected to said computer processor, said computer processor receiving said patient case information from said first tangible repository, said computer processor analyzing said patient case information to identify semantic concepts by recognizing phrases in said patient case information logically related to medical concepts, and generating a query by automatically supplying said semantic concepts to blank slots in a query template to generate said query, said query comprising a medical question, said computer processor generating answers to said query by applying natural language processing techniques to match said query to passages of said medical domain knowledge within said evidence sources, said evidence sources comprising information in unstructured form, said computer processor calculating numerical values of evidence dimensions for each of said answers by assigning different numerical values to each of said answers based on the correctness of each of said answers for different semantic concepts, said computer processor calculating corresponding confidence values for said answers by combining said numerical values of said evidence dimensions as calculated for said answer, said computer processor outputting, concurrently by said decision-support system to a decision-maker for said patient, said answers, said numerical values of said evidence dimensions for each of said answers, said corresponding confidence values for said answers, and at least one automatically generated link to said evidence sources for each of said answers so that said answers, said numerical values of said evidence dimensions for each of said answers, said corresponding confidence values for said answers, and said evidence sources for each of said answers are usable by said decision-maker to make a decision regarding said patient, said computer processor further storing, in said second tangible repository, said answers, said numerical values of said evidence dimensions for each of said answers, and said corresponding confidence values for said answers, said computer processor further, in response to new medical domain knowledge being added to said evidence sources, automatically repeating said generating of said answers to said query, said calculating of said numerical values of said evidence dimensions for each of said answers and said calculating of said corresponding confidence values for said answers in order to determine whether previously generated answers and corresponding confidence values stored in said second tangible repository would change based on said new medical domain knowledge, and said computer processor automatically sending an alert to said decision-maker based on a change occurring in any of said previously generated answers and corresponding confidence values, said alert being usable by said decision-maker to re-evaluate said decision.

13. The system according to claim 12, said computer processor further automatically repeating said generating of said query, said generating of said answers to said query, said calculating of said numerical values of said evidence dimensions for each of said answers, and said calculating of said corresponding confidence values for said answers based on new patient case information being received.

14. The system according to claim 12, further comprising a third tangible repository for maintaining medical domain knowledge content, said computer processor generating said answers by analyzing said medical domain knowledge content.

15. The system according to claim 12, said computer processor generating said query being carried out by said computer processor receiving said query as an input in a form of at least one of a free-form query, a free-form statement, and keyword search.

16. The system according to claim 12, said computer processor outputting a piece of evidence supporting a selected evidence dimension and an associated provenance for said piece of evidence.

17. The system according to claim 16, said computer processor removing a selected piece of evidence from said evidence sources contributing to a numerical value of an evidence dimension of a specific answer, recalculating said numerical value of said evidence dimension of said specific answer having said selected piece of evidence removed to produce a recalculated numerical value, and recalculating a new confidence value of said specific answer based on said recalculated numerical value.

18. The system according to claim 12, said computer processor identifying information relevant to said answers that is not contained within said patient case information as missing information and outputting a request to said decision-maker to add said missing information to said patient case information.

19. The system according to claim 18, said computer processor identifying an amount said missing information affects corresponding confidence values of said answers.

20. A computer program product comprising a tangible computer readable storage device storing computer readable program code comprising instructions executable by a computerized device, said computerized device having access to evidence sources containing medical domain knowledge and said computer program code comprising:

an input/output module receiving patient case information regarding a patient; a patient case analysis module analyzing said patient case information to identify semantic concepts by recognizing phrases in said patient case information logically related to medical concepts;

a question generation module generating a query by automatically supplying said semantic concepts to blank slots in a query template to generate said query, said query comprising a medical question; and a question-answering module generating answers to said query by applying natural language processing techniques to match said query to passages of said medical domain knowledge within said evidence sources, said evidence sources comprising information in unstructured form, said question-answering module calculating numerical values of evidence dimensions for each of said answers by assigning different numerical values to each of said answers based on the correctness of each of said answers for different semantic concepts, said question-answering module calculating corresponding confidence values for said answers by combining said numerical values of said evidence dimensions as calculated for said answer, said input/output module outputting, concurrently by said decision-support system to a decision-maker for said patient, said answers, said numerical values of said evidence dimensions for each of said answers, said corresponding confidence values for said answers, and at least one automatically generated link to said evidence sources for each of said answers so that said answers, said numerical values of said evidence dimensions for each of said answers, said corresponding confidence values for said answers, and said evidence sources for each of said answers are usable by said decision-maker to make a decision regarding said patient, said input/output module further storing, said answers, said numerical values of said evidence dimensions for each of said answers and said corresponding confidence values for said answers in a tangible repository, said question-answering module further, in response to new medical domain knowledge being added to said evidence sources, automatically repeating said generating of said answers, said calculating of said numerical values of said evidence dimensions for each of said answers and said calculating of said corresponding confidence values for said answers to determine whether previously generated answers and corresponding confidence values stored in said tangible repository would change based on said new medical domain knowledge, and said input/output module automatically sending an alert to said decision-maker based on a change occurring in any of said previously generated answers and corresponding confidence, said alert being usable by said decision-maker to re-evaluate said decision.

* * * * *